United States Patent
Xiao

(10) Patent No.: US 7,183,257 B2
(45) Date of Patent: Feb. 27, 2007

(54) USE OF RPL41 TO TREAT INFECTIONS AND INHIBIT CANCER

(75) Inventor: Sheng Xiao, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 11/105,179

(22) Filed: Apr. 13, 2005

(65) Prior Publication Data

US 2005/0277591 A1 Dec. 15, 2005

Related U.S. Application Data

(60) Provisional application No. 60/562,142, filed on Apr. 14, 2004, provisional application No. 60/605,436, filed on Aug. 30, 2004.

(51) Int. Cl.
*A01N 37/16* (2006.01)

(52) U.S. Cl. ......................................... 514/12; 530/324

(58) Field of Classification Search ..................... None
See application file for complete search history.

(56) References Cited

U.S. PATENT DOCUMENTS

2002/0051978 A1* 5/2002 Roth et al. ..................... 435/6

OTHER PUBLICATIONS

Ahmed et al., "Significance of protein kinase CK1 nuclear signaling in neoplasia," *J. Cell Biochem. Suppl.*, 35:130-135, 2000.
Amsterdam et al., "Many ribosomal protein genes are cancer genes in zebrafish," *PLoS. Biol.*, 2:E139, 2004.
Becker-Hapak et al., "TAT-Mediated protein transduction into mammalian cells," *Methods*, 24:247-256, 2001.
Denicourt and Dowdy, "Protein transduction technology offers novel therapeutic approach for brain ischemia," *Trends Pharmacol. Sci.*, 24:216-218, 2003.
Faust et al., "Antisense oligonucleotides against protein kinase CK2-a inhibit growth of squamous cell carcinoma of the head and neck in vitro," *Head Neck,* 22:341-346, 2000.
GenBank Accession No. AJ001347.
GenBank Accession No. NM_021104.
GenBank Accession No. X16066.
Go and Taniguchi, "Augmentation in the expression of a ribosomal protein associated with transformation," *Biochem. Mol. Biol. Int.*, 46(3):629-638, 1998.
Klaudiny et al., "Characterization by cDNA cloning of the mRNA of a highly basic human protein homologous to the yeast ribosomal protein YL41," *Biochem. Biophys. Res. Commun.*, 187(2):901-906, 1992.
Lee et al., "The highly basic ribosomal protein L41 interacts with the B subunit of protein kinase CKII and stimulates phosphorylation of DNA topoisomerase IIa by CKII," *Biochem. Biophys. Res. Commun.*, 238-(2):462-467, 1997.
Mutoh et al., "A gene coding for a ribosomal protein L41 in cycloheximide-resistant ribosomes has a promoter which is upregulated under the growth-inhibitory conditions in yeast, Candida maltosa," *Biochem. Biophys. Res. Commun.*, 258(3):611-615, 1999.
Schwarze et al., "Protein transduction: unrestricted delivery into all cells?," *Trends Cell Biol.*, 10:290-295, 2000.
Suzuki et al., "Yeast ribosomal proteins: XI> Molecular analysis of two genes encoding YL41, and extremely small basic ribosomal protein, from *Saccharomyces cerevisiae*," *Curr. Genet.*, 17(3):185-190, 1990.
Tallada et al., "Genome-wide search of Schizosaccharomyces pombe genes causing overexpression-mediated cell cycle defects," *Yeast*, 19(13):1139-1151, 2002.
Wender et al., "The design, synthesis, and evaluation of molecules that enable or enhance cellular uptake: Peptoid molecular transporters," *Proc. Natl. Acad. Sci. USA*, 97:13003-13008, 2000.
Woo and Hawes, "Cloning of genes whose expression is correlated with mitosis and localized in dividing cells in root caps of Pisum sativum L.," *Plant Mol. Biol.*, 35(6):1045-1051, 1997.
Yu and Warner,"Expression of a micro-protein," *J. Biol. Chem.*, 276(36);33821-33852, 2001.

* cited by examiner

*Primary Examiner*—Anish Gupta
*Assistant Examiner*—Satyanarayana R. Gudibande
(74) *Attorney, Agent, or Firm*—Fulbright & Jaworski

(57) ABSTRACT

The present invention relates to peptides of RPL41 and their use in the treatment of cancer and microbial infections. It is contemplated that modified forms of RPL41, including substitutional variants and mimetics, will be used. Mono- and combination therapies with other cancer treatments are contemplated.

2 Claims, 13 Drawing Sheets

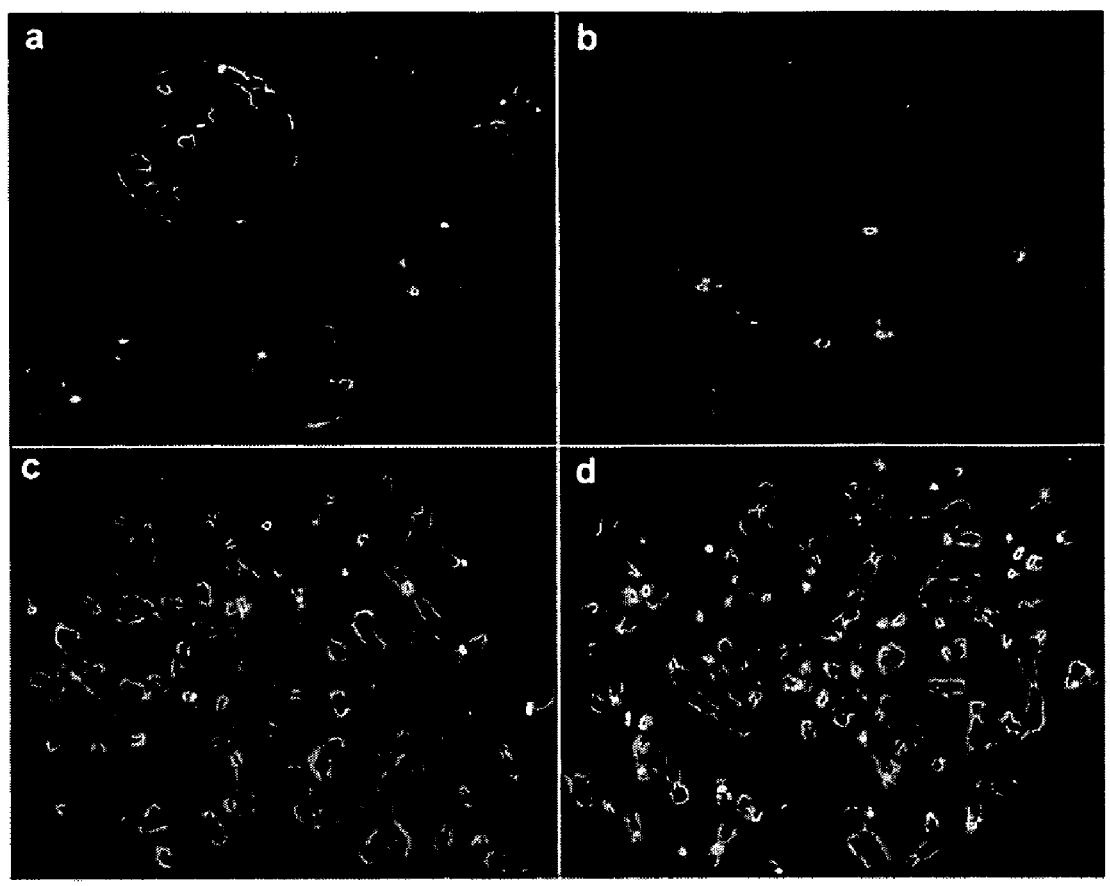
FIG. 3A-D

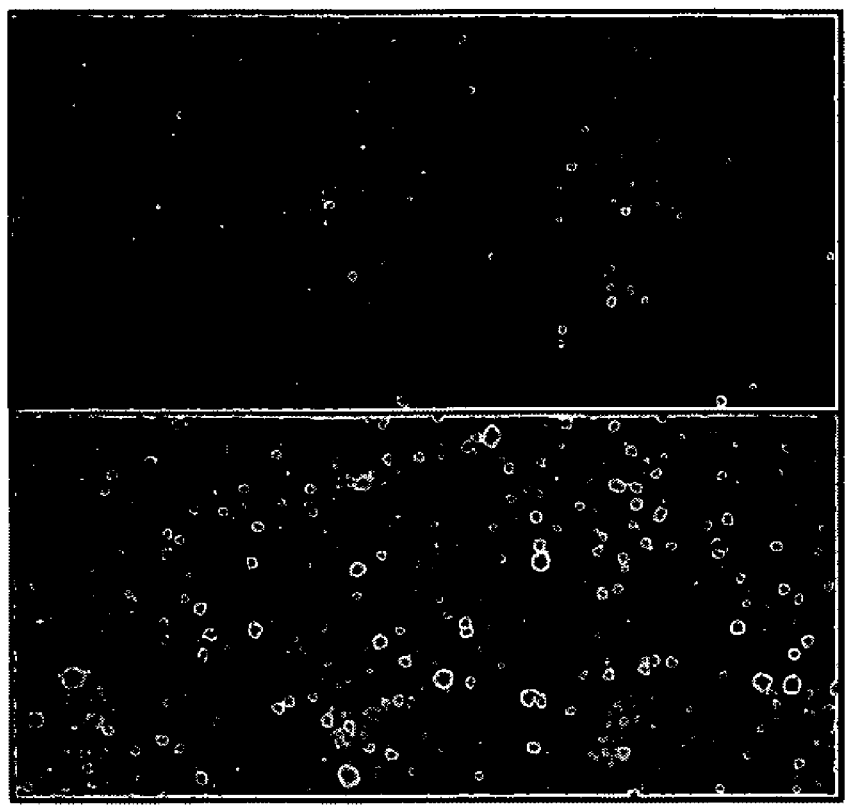
| Cases | Number of colonies in soft agar plates | |
|---|---|---|
| | Cells expressing RPL41 | Control cells |
| MCF7 | 23 | 207 |
| HTB81 | 19 | 257 |
| CRL5803 | 34 | 213 |
FIG. 4A-B

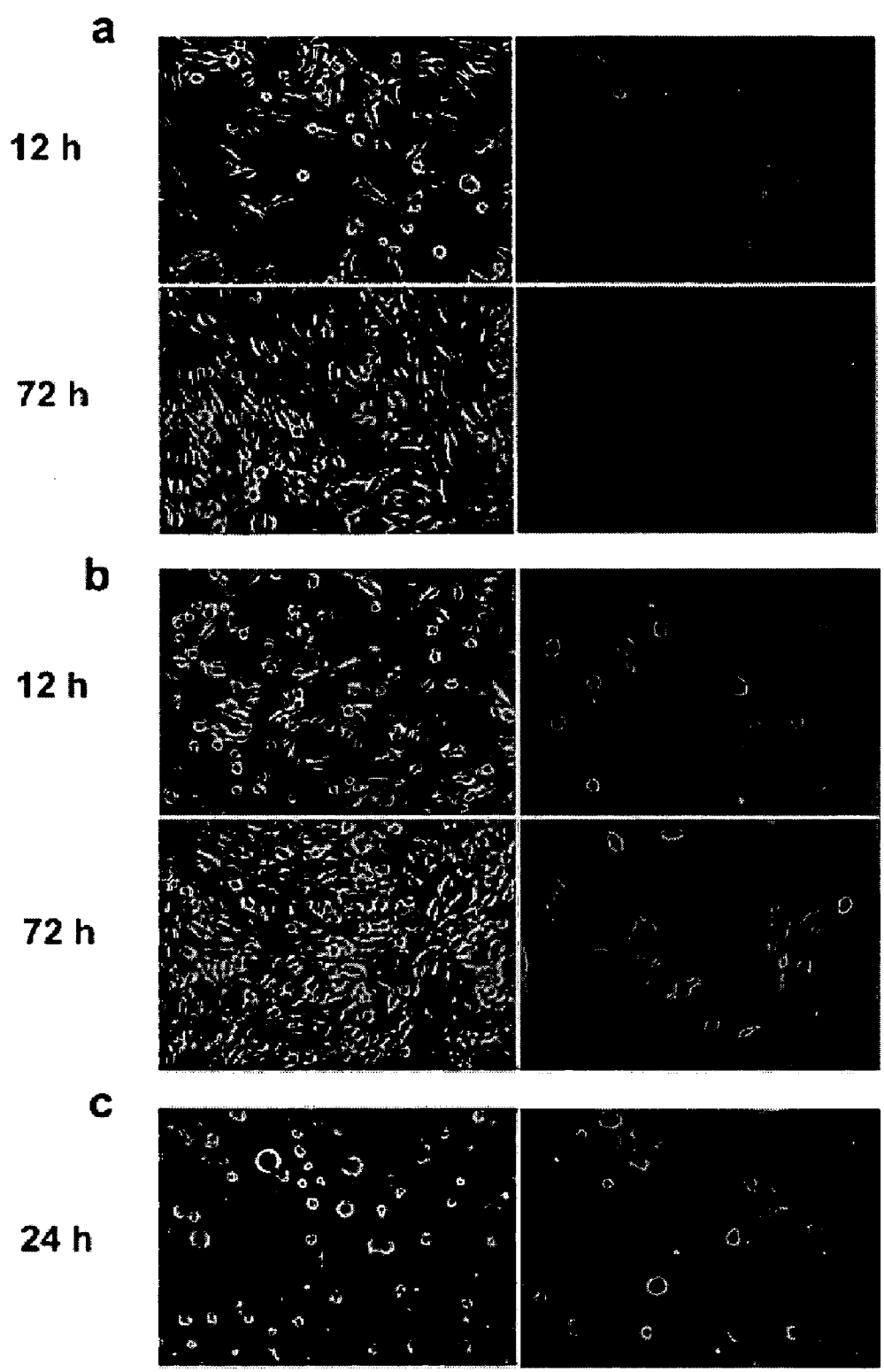
FIG. 5A-C

A
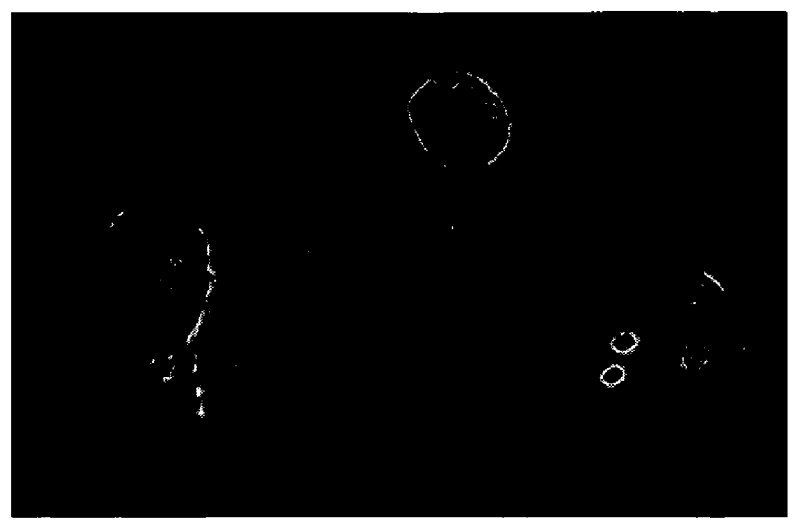
B
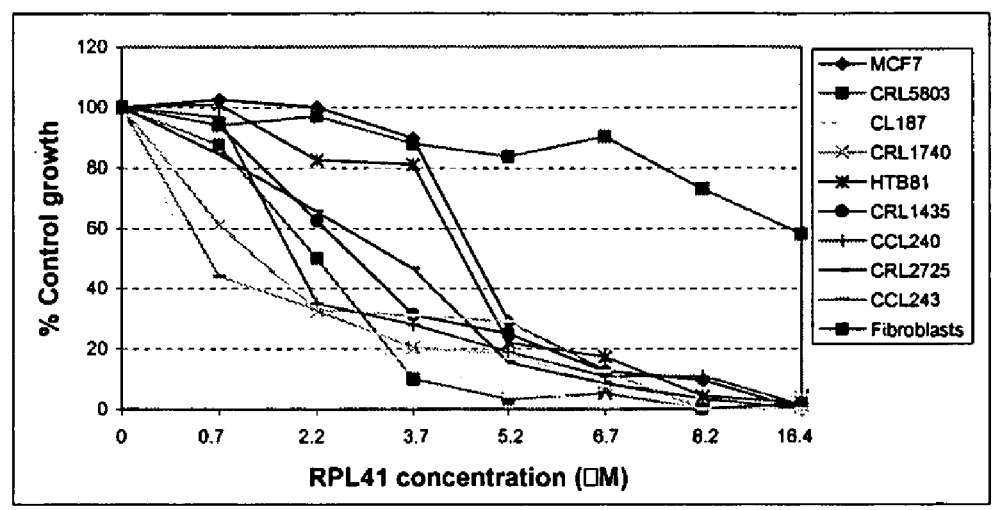
FIG. 6A-B

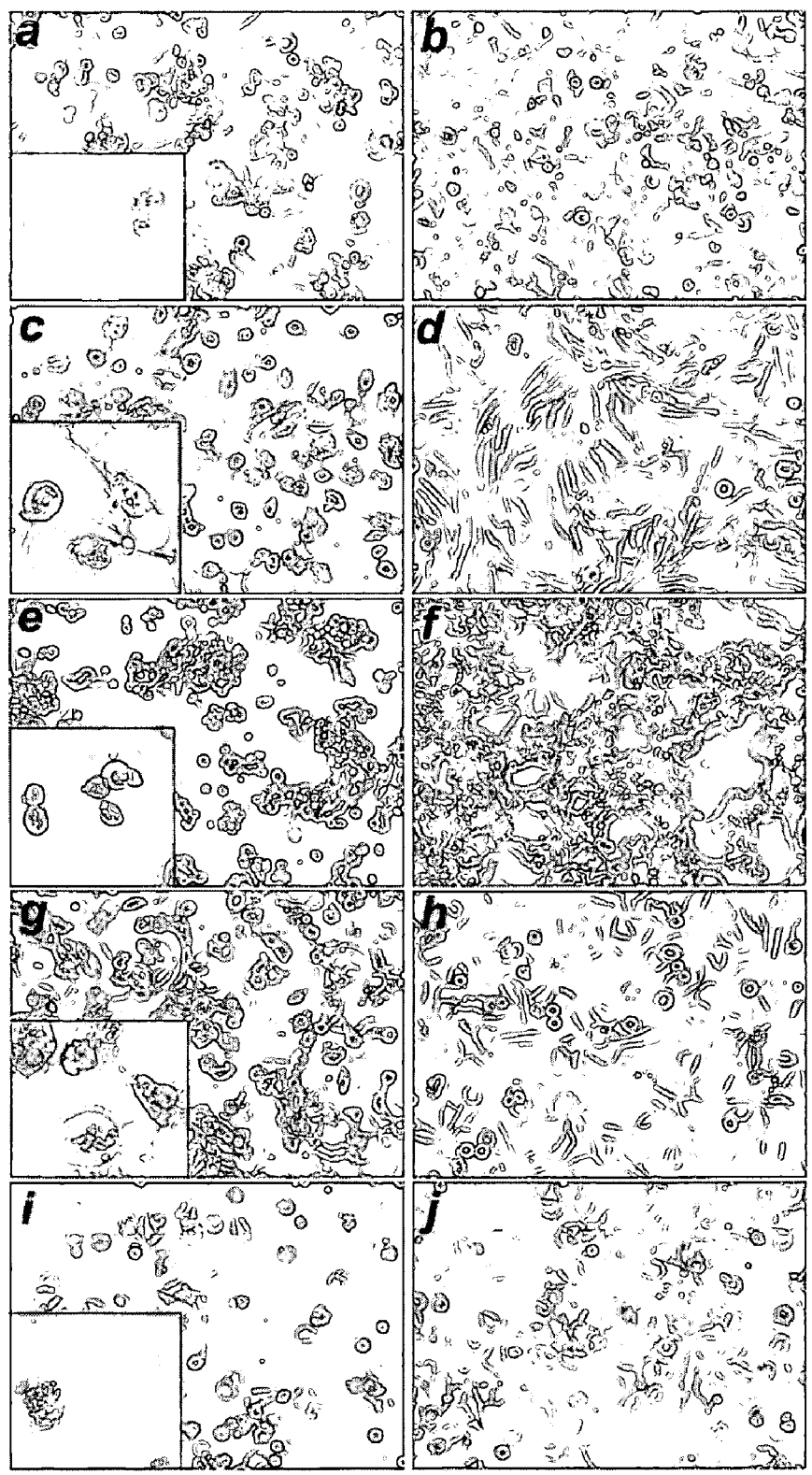
FIG. 7A-J

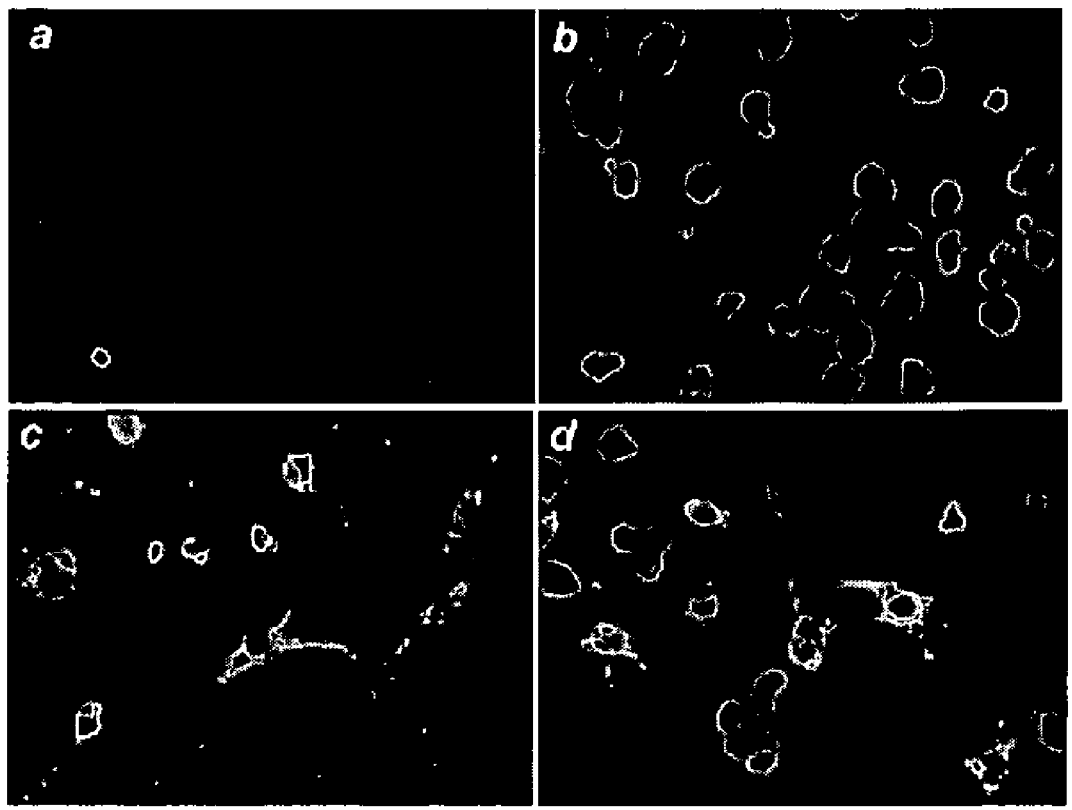
FIG. 8A-D

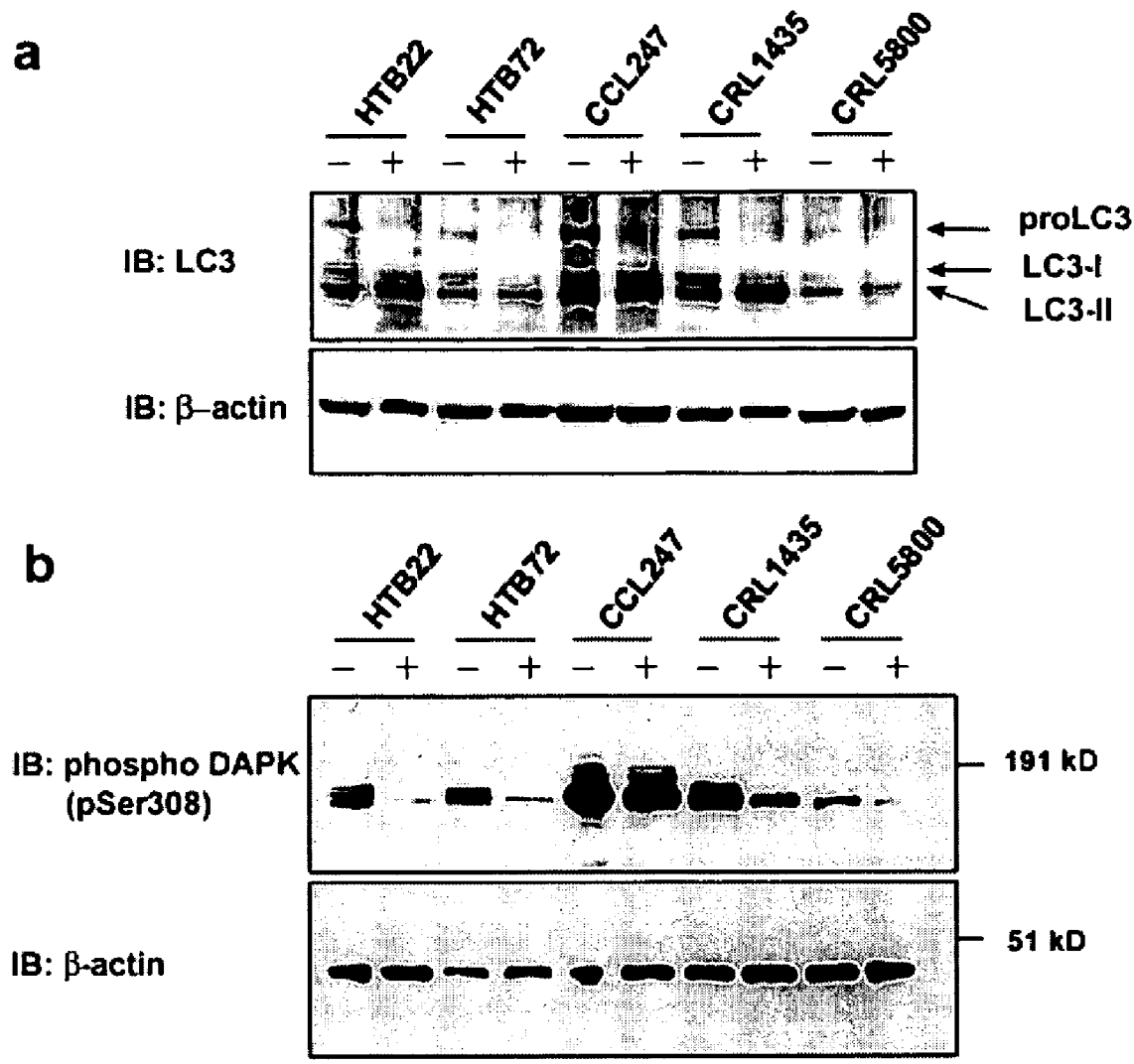
FIG. 11A-B

A
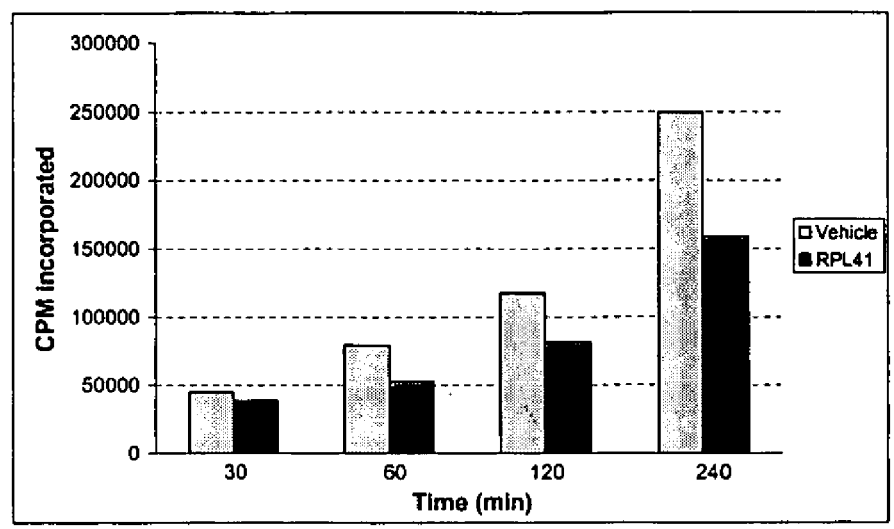
B
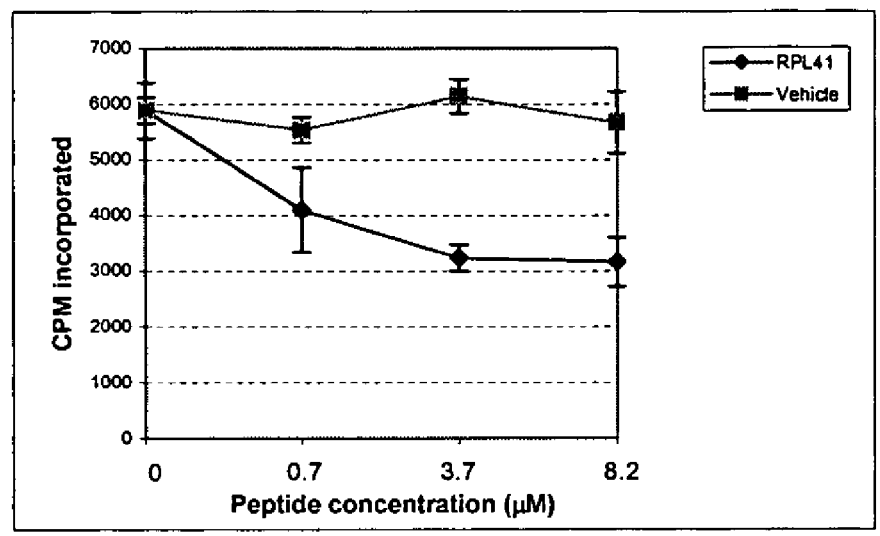
FIG. 12A-B

A
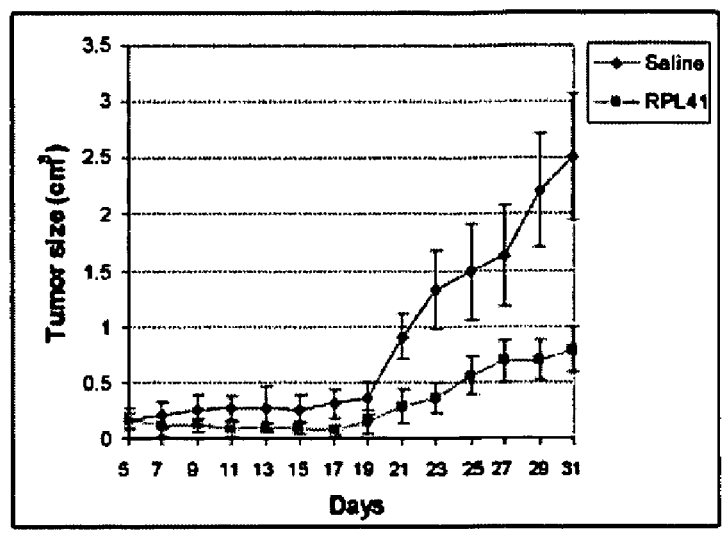
B
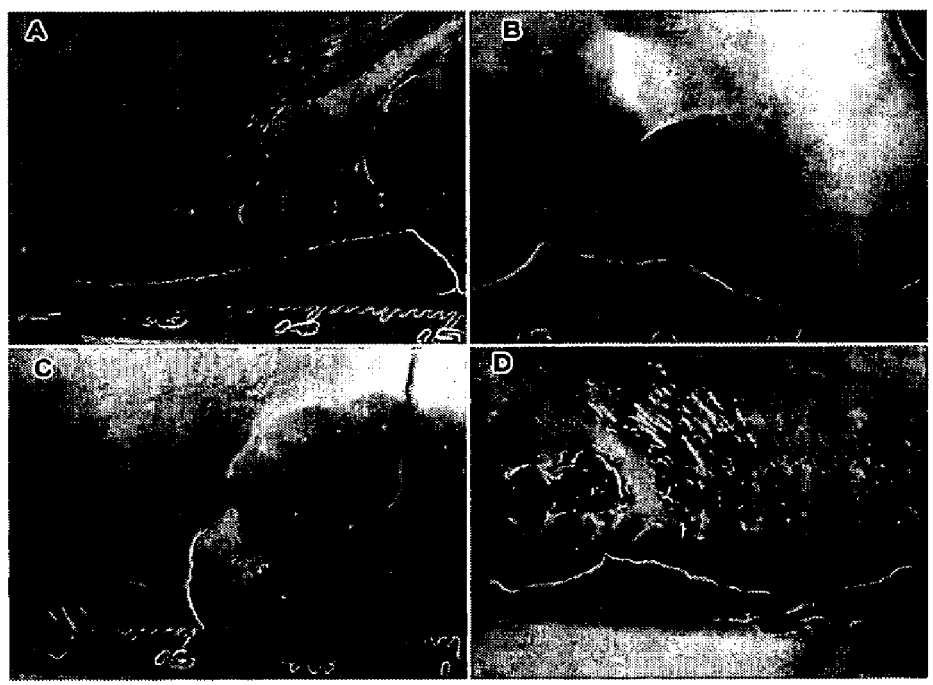
FIG. 13A-B

USE OF RPL41 TO TREAT INFECTIONS
AND INHIBIT CANCER

This application is related to U.S. Provisional Ser. No. 60/562,142, filed Apr. 14, 2004, and U.S. Provisional Application Ser. No. 60/605,436, filed Aug. 30, 2004, the entire contents of which are hereby incorporated by reference.

BACKGROUND OF THE INVENTION

1. Field of the Invention

The present invention relates to fields of molecular biology, microbiology and oncology. More particularly, the present invention relates to RPL41 and methods of use in the treatment of cancer and microbial infections 2. Description of Related Art Normal tissue homeostasis is a highly regulated process of cell proliferation and cell death. An imbalance of either cell proliferation or cell death can develop into a cancerous state. For example, cervical, kidney, lung, pancreatic, colorectal and brain cancer are just a few examples of the many cancers that can result (Erlandsson, 1998; Kolmel, 1998; Mangray and King, 1998; Mougin et al., 1998). In fact, the occurrence of cancer is so high that over 500,000 deaths per year are attributed to cancer in the United States alone.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken. Radiation therapy, chemotherapy and immunotherapy are alternatives to surgical treatment of cancer (Mayer, 1998; Ohara, 1998; Ho et al., 1998). Radiation therapy involves a precise aiming of high energy radiation to destroy cancer cells and much like surgery, is mainly effective in the treatment of non-metastasized, localized cancer cells. Side effects of radiation therapy include skin irritation, difficulty swallowing, dry mouth, nausea, diarrhea, hair loss and loss of energy (Curran, 1998; Brizel, 1998).

Chemotherapy, the treatment of cancer with anti-cancer drugs, is another mode of cancer therapy. The effectiveness of a given anti-cancer drug therapy often is limited by the difficulty of achieving drug delivery throughout solid tumors (el-Kareh and Secomb, 1997). Chemotherapeutic strategies are based on tumor tissue growth, wherein the anti-cancer drug is targeted to the rapidly dividing cancer cells. Most chemotherapy approaches include the combination of more than one anti-cancer drug, which has proven to increase the response rate of a wide variety of cancers (U.S. Pat. Nos. 5,824,348; 5,633,016 and 5,798,339, incorporated herein by reference). A major side effect of chemotherapy drugs is that they also affect normal tissue cells, with the cells most likely to be affected being those that divide rapidly (e.g., bone marrow, gastrointestinal tract, reproductive system and hair follicles). Other toxic side effects of chemotherapy drugs are sores in the mouth, difficulty swallowing, dry mouth, nausea, diarrhea, vomiting, fatigue, bleeding, hair loss and infection.

Additional therapies relying on biologic intervention (immunotherapy, hormonal therapy, gene therapy, anti-tumor antibodies) constitute a rapidly evolving area in cancer research, is yet another option for the treatment of certain types of malignancies. Unfortunately, few of these have progressed to the point of clinical application. Thus, there remains an intense need to discover new and improved therapeutic interventions in the treatment of human cancer.

SUMMARY OF THE INVENTION

Thus, in accordance with the present invention, there is provided an RPL41 peptide comprising the sequence MRAKWRKKRMRRLKRKRRKMRQRSK (SEQ ID NO:1), or conservative variants thereof, further comprising at least one of (a) a non-natural amino acid; (b) a stabilizing polymer; (c) a label; (d) a drug; or (e) a cellular or subcellular localization signal. The peptide may be 25 residues in length, 30 residues in length, 35 residues in length, 40 residues in length or 50 residues in length. Also provided is a pharmaceutical composition comprising an RPL41 peptide comprising the sequence of SEQ ID NO:1, or conservative variants thereof, dispersed in a pharmaceutically acceptable buffer, diluent or excipient.

In another embodiment, there is provided a method of inducing apoptosis in a cancer cell comprising contacting said cancer cell with an RPL41 peptide. The peptide may be 25 to no more than 50 residues and comprise the sequence of SEQ ID NO:1, or conservative variants thereof. The cancer cell may be a lung cancer cell, a breast cancer cell, an ovarian cancer cell, a uterine cancer cell, a cervical cancer cell, a prostate cancer cell, a stomach cancer cell, a colon cancer cell, an esophageal cancer cell, a head & neck cancer cell, a brain cancer cell, a liver cancer cell, a pancreatic cancer cell, a testicular cancer cell, a skin cancer cell, a blood cancer cell or a lymphatic cancer cell. The peptide may further comprise a cellular or subcellular localization signal, at least one non-natural amino acid, and/or be linked to a stabilizing polymer.

The peptide may be comprised within a lipid delivery vehicle, such as a liposome. Alternatively, the peptide may be contacted with said cell by transferring an expression construct encoding said peptide or polypeptide into said cell, such as a viral vector. A viral vector includes an adenoviral vector, an adeno-associated viral vector, a retroviral vector, a polyoma viral vector, a herpesviral vector, or a pox viral vector. Also contemplated are a non-viral vectors, such as those comprised within a lipid delivery vehicle. The expression construct may comprise a nucleic acid sequence comprising the sequence of atgagagccaagtggaggaagaagcgaatgcgcaggctgaagcgcaaaagaagaaagatgaggcagaggtccaagtaa (SEQ ID NO:2).

The method may further comprise contacting said cancer cell with a second anti-cancer treatment, such as radiation, chemotherapy, immunotherapy, gene therapy, or hormonal therapy. The second anticancer treatment is contacted with said cancer cell before said peptide, after said peptide, or at the same time as said peptide. The cancer cell may be contacted with said peptide more than once.

In yet another embodiment, there is provided a method of treating a subject with cancer comprising administering to said subject an RPL41 peptide. The peptide may be conjugated to a stabilizing polymer, a drug or a label. The peptide may be 25 to no more than 50 residues and comprising the sequence of SEQ ID NO:1, or conservative variants thereof. The cancer may be lung cancer, breast cancer, ovarian cancer, uterine cancer, cervical cancer, prostate cancer, stomach cancer, colon cancer, esophageal cancer, head & neck cancer, brain cancer, liver cancer, pancreatic cancer, testicular cancer, skin cancer, blood cancer or lymphatic cancer.

The peptide may be comprised within a lipid delivery vehicle, such as a liposome. The method may further comprise administering to said subject a second anti-cancer treatment, such as radiation, chemotherapy, immunotherapy, gene therapy, hormonal therapy or surgery. The peptide may be administered subcutaneously, intravenously, intra-arterially, local to a tumor, regional to a tumor, systemically or intratumorally. The peptide may be administered more than once. The peptide may be 25 to no more than 50 residues and comprise the sequence of SEQ ID NO:1, or conservative variants thereof.

In still yet another embodiment, there is provided a method of treating a subject with cancer comprising administering to said subject an expression construct encoding an RPL41 peptide into said cell. The expression construct may be a viral vector, such as an adenoviral vector, an adeno-associated viral vector, a retroviral vector, a polyoma viral vector, a herpesviral vector, or a pox viral vector. The expression construct may also be a non-viral vector, which may be comprised within a lipid delivery vehicle, such as a liposome.

The cancer may be lung cancer, breast cancer, ovarian cancer, uterine cancer, cervical cancer, prostate cancer, stomach cancer, colon cancer, esophageal cancer, head & neck cancer, brain cancer, liver cancer, pancreatic cancer, testicular cancer, skin cancer, blood cancer or lymphatic cancer. The method may further comprise administering to said subject a second anti-cancer treatment, such as radiation, chemotherapy, immunotherapy, gene therapy, hormonal therapy or surgery. The expression construct may be administered subcutaneously, intravenously, intra-arterially, local to a tumor, regional to a tumor, systemically or intratumorally. The expression construct may be administered more than once.

Other embodimements include a peptidomimetic of a peptide comprising the sequence of SEQ ID NO:1, and a peptide comprising entirely D amino acids and comprising the sequence of KSRQRMKRRKRKLRRM-RKKRWKARM (SEQ ID NO:3).

In still a further embodiment, there is provided a method of treating an infection in a subject comprising administering to said subject an RPL41 peptide or an expression vector encoding therefor. The peptide may be 25 to no more than 50 residues and comprises the sequence of SEQ ID NO:1, or conservative variants thereof. The infection may be a bacterial infection, a fungal infection or a viral infection. The peptide may be comprised within a lipid delivery vehicle, such as a liposome. The expression construct may be a viral vector, such as an adenoviral vector, an adeno-associated viral vector, a retroviral vector, a polyoma viral vector, a herpesviral vector, or a pox viral vector. Alternatively, the expression construct may be a non-viral vector, for example, one that is comprised within a lipid delivery vehicle. The method may further comprise administering to said subject a second anti-cancer anti-microbial agent. The peptide may further comprises a cellular or subcellular localization signal, at least one non-natural amino acid, and/or a stabilizing polymer. The peptide or expression construct may be administered more than once.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWING

The following drawings form part of the present specification and are included to further demonstrate certain aspects of the present invention. The invention may be better understood by reference to one or more of these drawings in combination with the detailed description of specific embodiments presented herein.

FIGS. 3A–D—FISH analysis with a RPL41 BAC clone (red) and a chromosome 12 centromere probe (green) showed RPL41 allelic reduction. (FIG. 3A) AML CCL-246. (FIG. 3B) Breast cancer CRL1500. (FIG. 3C) Prostate cancer CRL1435. (FIG. 3D) Lung adenocarcinoma CRL5803.

FIGS. 4A–B—Overexpression of RPL41 in tumor cells resulted in the inhibition of anchorage-independent growth in soft agar. (FIG. 4A) Prostate cancer cells (HTB81) were transfected with a RPL41 expression construct (top) or an empty vector (bottom), selected in the presence of neomycin for two weeks, and planted in 35-mm plates containing 0.3% agar and cultured for two weeks. Colonies were fixed with methanol and stained with Giemsa. (FIG. 4B) Colonies that exceeded 120 µm in diameter in soft agar plates for breast cancer cells (MCF7), prostate cancer cells (HTB81), and lung cancer cells (CRL5803) expressing RPL41 or vector only were counted. The number of colonies is the average value based on six dishes in two independent experiments.

FIGS. 5A–C—Inhibition of tumor cell growth by over-expressing RPL41/GFP. Malignant melanoma cells (HTB72) were transfected with a RPL41/GFP construct (FIG. 5A) or GFP only vector (FIG. 5B). Transfection efficiency was similar for both RPL41/GFP and GFP constructs at approximately 40–50%. Three days after transfection, cells overexpressing RPL41/GFP were mostly replaced by those GFP negative cells (non-transfected cells or cells expressing lower lever RPL41/GFP), in the absence of neomycin selection; No such selection was observed in cells overexpressing GFP vector. Similar results were observed in the remaining four tumor cell lines (data not shown) (c) Tumor cells (CRL5800) overexpressing RPL41/GFP showed cell shrinkage and membrane blebbing 24 hours after transfection.

FIGS. 6A–B—Inhibition of tumor cell growth by a synthetic RPL41. (FIG. 6A) An FITC-labeled RPL41 was incubated with cells for 15 minutes; cells were then washed and counterstained (nuclei) with DAPI. FITC-RPL41 was observed in nucleoli as well as in cytoplasmic granules. (FIG. 6B) Nine tumor cell lines, including a breast cancer (MCF7), a lung cancer (CRL5803), a colon cancer (CL187), 3 prostate cancers (CRL1740, HTB81 and CRL1435), an APML (CCL240), an AML (CRL2725), and a CML (CCL243), and normal fibroblasts were treated with synthetic RPL41 at various concentrations. Cell growth relative to that of vehicle controls was determined. The concentration of the synthetic RPL41 peptide was determined by a Bio-Rad Protein Assay kit. Similar inhibition effect by RPL41 was also observed in the remaining 15 cell lines studied (data not shown).

FIGS. 7A–J—Morphologic changes of tumor cells treated with RPL41 peptide. Five tumor cell lines, including breast cancer MCF7 (FIGS. 7A & B), malignant melanoma HTB72 (FIGS. 7C & D), colon cancer HCT116 (FIGS. 7E & F), prostate cancer CRL1435 (FIGS. 7G & H), lung cancer CRL5800 (FIGS. 7I & J), were treated with RPL41 peptide (6.7 µM) (left panel) or vehicle control (right panel) for 8 hours. The inserts showed cells with membrane blebbing, a phenomenon peaked at 6–8 hours after RPL41 administration.

FIGS. 8A–D—Tumor cells treated with RPL41 peptide were TNNEL positive with the involvement of mitochondrial pathway. Lung cancer cells (CRL5800) were cultured in chamber slides, treated with RPL41 (6.7 µM) (FIGS. 8B & D) or vehicle control (FIGS. 8A & C) for 8 hours and subjected to TUNEL assay and mitochondrial transmembrane potential ($\Delta\psi_m$) assay. TUNEL positive cells were those with bright green fluorescence; $\Delta\psi_m$ positive cells were those with green fluorescence with no red signals.

FIGS. 11A–B—Activation of MAP1LC3 and DAPk in RPL41 treated cells. Five tumor cell lines, including malignant melanoma HTB72, prostate cancer CRL1435, lung cancer CRL5800, colon cancer HCT116, breast cancer MCF7, were treated with RPL41 peptide (6.7 µM)(+) or vehicle control (−) overnight and immunoblotted with an antibody specific to proLC3/LC3-I/LC3-I (FIG. 11A) or Ser308 phosphorylated DAPk (FIG. 11B). RPL41 treated cells showed consistent decrease on proLC3 and LC3-I; some had increased LC3-II. RPL41 treated cells also showed significant dephosphorylation of Ser308. Immunoblots were also stained with an antibody to β-actin.

FIGS. 12A–B—RPL41 inhibited protein synthesis and CK2 activity. (FIG. 12A) Quiesced lung cancer cells (CRL5800) were stimulated with FBS and treated with RPL41 (6.7 µM) or vehicle control in the presence of [$^{35}$S]methionine for 30, 60, 120, 240 minutes. Cells were harvested and measured by scintillation counting. (FIG. 12B) Tumor cells (CRL5800) were treated with various concentrations of RPL41 or vehicle control for 30 minutes and subjected to CK2 assay with a CK2-specific substrate in the presence of [γ-$^{32}$P]ATP. Phosphorylated substrate was measured by scintillation counting. The number of CPM incorporated is the average value based on three independent experiments.

FIGS. 13A–B—Inhibition of mice tumor by RPL41. (FIG. 13A) Nude mice carrying HCT116 colon cancers (five per group) were treated by intraperitoneal injections of 0.5 ml saline solution or RPL41 (7.5 mg/kg per day in 0.5 ml of saline solution) on days 5–24 after inoculation with tumor cells. The length (L) and width (W) of tumors were determined with a caliper. Tumor sizes were calculated by the following formula: $cm^3 = (L \times W^2) \times 0.52$. Results are presented as mean tumor volume±s.d. (FIG. 13B) Nude mice carrying CRL5803 lung cancers were treated by intra-tumor injections of 0.5 ml saline solution (left panel) or RPL41 (30 mg/kg per day in 0.5 ml of saline solution) (right panel) for continuous two days. Tumors were measured and photographed 4 weeks after treatment.

DESCRIPTION OF ILLUSTRATIVE EMBODIMENTS

1. RPL41 Peptides and Polypeptides

Figure 1:
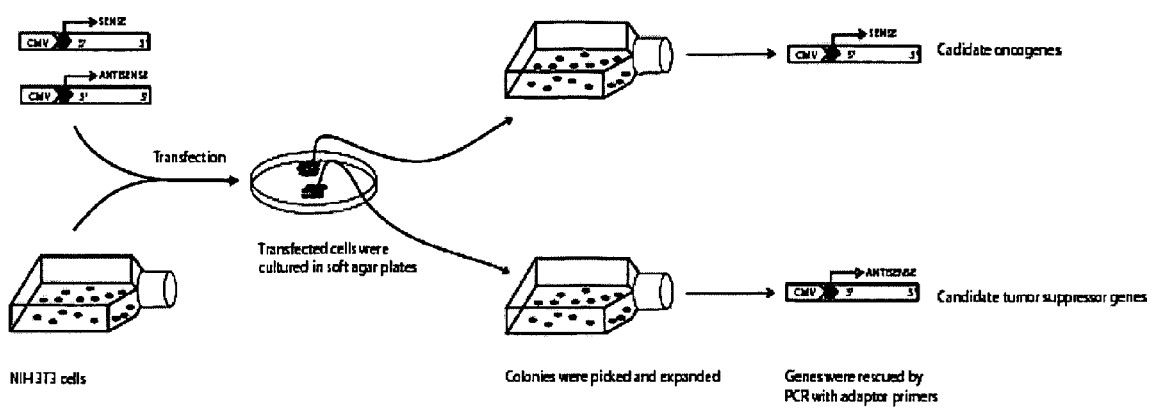
FIG. 1—Experimental strategy for functional screening of transforming genes. Tumor genes were expressed in non-neoplastic NIH3T3 cells in both sense and antisense orientation. Transformed 3T3 cells were identified by their capabilities of anchorage-independent growth. Transforming genes were rescued and sequenced. Depending on the expression orientation of transcripts, transforming genes were identified as candidate oncogenes or tumor suppressor genes.

The present invention relates to the use of RPL41. RPL41 is a highly basic ribosomal protein that bears significant homology to the yeast YL41 ribosomal protein. It has been shown to interact with the beta subunit of casein kinase II (CKII), a heterotetramer composed of two catalytic (alpha and alpha') and two regulatory (beta and beta') subunits.

A. Structural Features

RPL41 peptides will comprise molecules of 5 to about 50 residues in length having the sequence MRAKWRKKRM-RRLKRKRRKMRQRSK (SEQ ID NO:1). A particular preferred length may be less than 35 residues, less than 30 residues, less than 25 residues, less than 20 residues, less than 15 residues, or less than 14, including 5, 6, 7, 8, 9, 10, 11, 12, or 13 residues. The peptides may be generated synthetically or by recombinant techniques, and are purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

The peptides may be labeled using various molecules, such as fluorescent, chromogenic or colorimetric agents. The peptides may also be linked to other molecules, including other anti-tumor agents. The links may be direct or through distinct linker molecules. The linker molecules in turn may be subject, in vivo, to cleavage, thereby releasing the agent from the peptide. Peptides may also be rendered multimeric by linking to larger, and possibly inert, carrier molecules.

Also contemplated for use are RPL41 homologs from other species such as yeast and qercus sober (accession nos. X16066 and AJ001347, respectively).

B. Variants or Analogs of RPL41 i. Substitutional Variants

It also is contemplated in the present invention that variants or analogs of RPL41 peptides may also inhibit tumor growth or microbial growth. Polypeptide sequence variants of RPL41, primarily making conservative amino acid substitutions to SEQ ID NO:1, may provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in RPL41 amino acid sequences and in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within±2 is preferred, those which are within±1 are particularly preferred, and those within±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within±2 is preferred, those that are within±1 are particularly preferred, and those within±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MBPs, but with altered and even improved characteristics.

ii. Altered Amino Acids

The present invention may employ peptides that comprise modified, non-natural and/or unusual amino acids. A table of exemplary, but not limiting, modified, non-natural and/or unusual amino acids is provided herein below. Chemical synthesis may be employed to incorporated such amino acids into the peptides of interest. Also, one or more D amino acids may be used to substitute with SEQ ID NO:1.

TABLE 1

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | Ahyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |

TABLE 1-continued

Modified, Non-Natural and Unusual Amino Acids

| Abbr. | Amino Acid | Abbr. | Amino Acid |
|---|---|---|---|
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | | iii. Mimetics

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins (Vita et al., 1998). A structural motif that appears to be evolutionarily conserved in certain toxins is small (30–40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

iv. D Amino Acids

In another form, the present invention contemplates use of variants that comprise various portions of an RPL41 peptide in reverse order of SEQ ID NO:1, using D amino acids, stereoisomers of natural amino acids which are in the L-form. KSRQRMKRRKRKLRRMRKKRWKARM (SEQ ID NO:3) illustrates the complete peptide sequence in reverse order. Just as with the L-form sequences, the inventor contemplates using molecules of 5 to about 50 residues in length. A particular preferred length may be less than 35 residues, less than 30 residues, less than 25 residues, less than 20 residues, less than 15 residues, or less than 13, including 5, 6, 7, 8, 9, 10, 11 or 12 residues. Also contemplated are labeled molecules, modified molecules, substitutional variants and mimetics.

C. Fusions and Modified Proteins

Another variant is a fusion protein. This molecule generally has all or a substantial portion of the original RPL41 molecule, linked at the N- or C-terminus, to all or a portion of a second peptide or polypeptide. For example, fusions may employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Of particular interest are peptide permeant motifs that improve peptides transfer through membranes. Such mofits include those from TAT and R9:

TAT=RKKRRQRRR (Schwarze et al., 2000; Becker-Hapak et al., 2001; Denicourt and Dowdy, 2003)

R9=RRRRRRRRR (Wender et al., 2000)

Localization sequences have been divided into routing signals, sorting signals, retention or salvage signals and membrane topology-stop transfer signals (Yellon et al., 1992). For example, there are signals to target the endoplasmic reticulum (Munro, et al., 1987), the nucleus (Lanford et al.,1986; Stanton et al., 1986; Harlow et al., 1985), the nucleolar region (Kubota et al., 1989; and Siomi et al., 1988), the endosomal compartment (Bakke et al., 1990), mitochondria (Yellon et al., 1992) and liposomes (Letoumeur et al., 1992). One preferred nuclear targeting sequence may be the SV40 nuclear localization signal.

Modified peptides also are contemplated. Non-sequence modifications include addition of various entities such as labels, drugs, and stabilizing agents (e.g., PEG, poly-L-lysine).

D. Purification of Proteins

It may be desirable to purify RPL41, variants, peptidemimics or analogs thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "–fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "–fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Peptide Synthesis

RPL41 and related peptides may be generated synthetically for use in various embodiments of the present invention. Because of their relatively small size, the peptides of the invention can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

2. RPL41 Nucleic Acids

Important aspects of the present invention concern isolated DNA segments and recombinant vectors encoding RPL41 and peptides thereof, the creation and use of recombinant host cells through the application of DNA technology, that express RPL41 or peptides thereof, and biologically functional equivalents thereof. Accession nos. for human, yeast and qercus sober RPL41 DNA sequences are NM-021104, X16066 and AJ00134, respectively.

The present invention concerns DNA segments, isolatable from mammalian cells, such as mouse, rat or human cells, that are free from total genomic DNA and that encode a RPL41 polypeptide or peptide. As used herein, the term "DNA segment" refers to a DNA molecule that has been isolated free of total genomic DNA of a particular species. Therefore, a DNA segment encoding RPL41 refers to a DNA segment that contains wild-type, polymorphic or mutant RPL41 coding sequences yet is isolated away from, or purified free from, total mammalian genomic DNA. Included within the term "DNA segment" are DNA segments and also recombinant vectors, including, for example, plasmids, cosmids, phage, viruses, and the like.

In particular embodiments, the invention concerns isolated DNA segments and recombinant vectors incorporating DNA sequences that encode a RPL41, a peptide, peptide-mimic or a biologically functional equivalent of a RPL41. The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:1 or any analog or variant thereof provided the biological activity of the protein is maintained. In particular embodiments, the biological activity of a RPL41 peptide, or a biologically functional equivalent, comprises binding to CKII.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. Screening Assays

The present invention also contemplates the screening of compounds, e.g., peptides, peptide-mimics, variants, analogs or small molecules, for various abilities to interact with CKII and/or inhibit or kill bacterial cells, and/or inhibit cancer cell growth or induce autophagic cell death in cancer cells. Particularly preferred compounds will be those that mimic the normal functions of the RPL41. In the screening assays of the present invention, the candidate substance may first be screened for basic biochemical activity—e.g., binding to a target molecule such as CKII—followed by subsequent testing for antibiotic and anti-cancer activity.

A. Modulators

The present invention provides methods of screening for agents that bind CKII. In an embodiment, the present invention is directed to a method of:

(a) providing a CKII polypeptide;

(b) contacting the CKII polypeptide with a putative RPL41 mimic; and (c) determining the binding of the mimic to the RPL41, wherein binding to RPL41 identifies the compound as an RPL41 mimic.

Measuring binding to CKII may be direct, by identifying a CKII-mimic complex, by identifying labeled mimic associated with CKII, or by assessing the inhibition of binding of a peptide comprising SEQ ID NO:1 to CKII by the mimic (competitive format). In still yet other embodiments, one would look at the effect of the mimic on bacteria, virus-infected cells or cancer cells.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like CKII or RPL41, and then design a molecule for its ability to interact with CKII or to mimic RPL41. This can be accomplished by x-ray crystallography, computer modeling or by a combination of both approaches.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as plants, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be a polypeptide, polynucleotide, small molecule inhibitor or any other compounds that may be designed through rational drug design starting from known inhibitors of hypertrophic response.

It will, of course, be understood that all the screening methods of the present invention are useful in themselves notwithstanding the fact that effective candidates may not be found. The invention provides methods for screening for such candidates, not solely methods of finding them.

B. In vitro Assays

A quick, inexpensive and easy assay to run is a CKII binding assay. Binding of a molecule to CKII may, in and of itself, be inhibitory, due to steric, allosteric or charge-charge interactions. This can be performed in solution or on a solid phase and can be utilized as a first round screen to rapidly eliminate certain compounds before moving into more sophisticated screening assays.

The target (e.g., CKII) may be either free in solution, fixed to a support, expressed in or on the surface of a cell. Either the target or the compound may be labeled, thereby permitting determination of binding. Competitive binding assays can be performed in which a peptide comprising SEQ ID NO:1 is used. The peptide may be labeled, or the candidate may be labeled. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. Bound polypeptide is detected by various methods.

C. In cyto Assays

Various bacterial or cancer cells may be used to screen RPL41 variants or mimics for antibiotic or anti-cancer activity. Exemplary cells include, but are not limited to [CRL5803 breast cancer cells]. Depending on the assay, culture may be required. Various readouts for inhibitory activity may be utilized, including cell staining, microscopy, TUNEL assays, and radioactive isotope incorporation assays.

D. In vivo Assays

The present invention particularly contemplates the use of various animal models. For example, various animal models of cancer or microbial infection may be used to determine if the RPL41 variants or putative mimics retain or even improve upon the antibiotic and/or anticancer activities of the wild-type molecule.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by oral, sublingual, intratracheal instillation, bronchial instillation, intradermal, subcutaneous, intramuscular, intraperitoneal, intratumoral, intralesional, or intravenous injection. Specifically contemplated are oral administration and systemic intravenous injection.

4. Engineering Expression Constructs

In certain embodiments, the present invention involves either the production of RPL41 peptides or the administration of a RPL41 nucleic acid to an animal. Such methods both rely upon expression constructs containing a RPL41 coding region and the means for its expression, plus elements that permit replication of the constructs. A variety of elements and vector types are discussed below.

A. Selectable Markers

In certain embodiments of the invention, expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal or chloramphenicol acetyltransferase (CAT).

B. Polyadenylation Signals

One will typically desire to include a polyadenylation signal to effect proper polyadenylation of the transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

C. Control Regions

Throughout this application, the term "expression construct" is meant to include any type of genetic construct containing a nucleic acid coding for the peptide of interest. The nucleic acid encoding the peptide is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

For the purpose of recombinant production, prokaryotic (bacteria) and lower eukaryotic organisms (yeast) are preferred. Commercial vectors and expression systems, including appropriate host cells and methods for transformation and culture, are well known to those of skill in the art.

In other embodmients, promoters refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters that are selectively active in neuronal tissues, such as dorsal root ganglion (DRG) neurons, nociceptive neurons may find particular utility in accordance with the present invention.

It is envisioned that any of the above promoters alone or in combination with another may be useful according to the present invention depending on the action desired. In addition, this list of promoters should not be construed to be exhaustive or limiting, those of skill in the art will know of other promoters that may be used in conjunction with the promoters and methods disclosed herein.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| PROMOTER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |

TABLE 2-continued

PROMOTER

Human Immunodeficiency Virus
Cytomegalovirus
Gibbon Ape Leukemia Virus

TABLE 3

| Element | Inducer |
| --- | --- |
| MTII | Phorbol Ester (TPA) |
|  | Heavy metals |
| MMTV (mouse mammary tumor virus) | Glucocorticoids |
| β-Interferon | Poly(rI)X |
|  | Poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

5. Methods of Gene Transfer

In order to effect recombinant expression of RPL41 peptide, it is necessary to transfer the appropriate expression construct into a host cell of interest. Such transfer may employ viral or non-viral methods of gene transfer. This section provides a discussion of methods and compositions of gene transfer.

A. Viral Vector-Mediated Transfer

In one embodiment of the invention, an expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses such as the papovaviruses (simian virus 40, bovine papilloma virus, and polyoma) (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. A wide variety of viruses are now used to succesfully transfer genetic material to eukaryotic cells.

In certain embodiments, the nucleic acid sequence is incorporated into a viral particle to mediate gene transfer to a cell. Typically, the virus simply will be exposed to the appropriate host cell under physiologic conditions, permitting uptake of the virus. The present methods may be advantageously employed using a variety of viral vectors, as discussed below.

i. Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) finction (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

ii. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed $\Psi$, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and $\Psi$ components is constructed (Mann et al., 1983). When a recombinant plasmid containing a human cDNA, together with the retroviral LTR and $\Psi$ sequences is introduced into this cell line (by calcium phosphate precipitation for example), the $\Psi$ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

iii. Adeno-associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996).

AAV-mediated efficient gene transfer and expression in the lung has led to clinical trials for the treatment of cystic fibrosis (Flotte and Carter, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

iv. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

B. Non-Viral Transfer

Several non-viral methods for the transfer of expression constructs into cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al., (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM also may be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

6. Methods of Treating Microbial Infection or Cancer

The present invention contemplates methods of treating various disease states such as cancer and bacterial/viral/fungal infection using RPL41 peptides, variants or mimetics. Two primary approaches may be applied. First, one may simply administer to the subject to be treated an RPL41 composition, such as a peptide, variant or mimic. Second, one may administer an expression construct that encodes and expresses an RPL41-related product. In either case, the subject is "contacted" with the product. In a further embodiment, the invention may rely on provision of the RPL41 product in combination with a second therapeutic agent.

A. Genetic Based Therapies

Specifically, the present inventors intend to provide, to a cell, an expression construct that expresses a RPL41 peptide or variant thereof. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

B. Protein Therapy

Another therapy approach is the provision, to a subject, of RPL41 peptides, synthetic or recombinant, or variants, mimetics or analogs thereof. Formulations would be selected based on the route of administration and purpose including, but not limited to, parenteral formulations, topical formulations, liposomal formulations and classic pharmaceutical preparations for oral administration.

C. Combined Antimicrobial Therapy

It is further contemplated that the RPL41 peptides, variants and mimics of the invention may be used in combination with or to enhance the activity of other antimicrobial agents or antibiotics. Combinations of the peptide with other agents may be useful to allow antibiotics to be used at lower doses due to toxicity concerns, to enhance the activity of antibiotics whose efficacy has been reduced or to effectuate a synergism between the components such that the combination is more effective than the sum of the efficacy of either component independently. Antibiotics which may be combined with a peptide in combination therapy include but are not limited to the antibiotics penicillin, ampicillin, amoxycillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraaminosalicylic acid, and ethambutol. Table 4 (Reese and Betts, 1991), lists the antibiotics generally preferred for use against a given pathogenic bacterium. It is contemplated that the effectiveness of all the antibiotics listed in Table 4 will be increased upon combination with an antimicrobial peptide. Table 5 (Reese and Betts, 1993), itemizes the common pathogenic bacteria that are implicated in focal infections. The present invention is thus contemplated for use against all such infections.

TABLE 4

ANTIBIOTICS OF CHOICE FOR COMMON PATHOGENS

| Pathogen | Antibiotic of First Choice[a] | Alternative Agents[a] |
|---|---|---|
| Gram-positive cocci | | |
| *Staphylococcus aureus* or *S. epidermidis* | | |
| Non-penicillinase-producing | Penicillin | A first-generation cephalosporin, vancomycin, imipenem, or clindamycin; a fluoroquinolone[b] |
| Penicillinase-producing | Penicillinase-resistant penicillin (e.g., oxacillin or nafcillin) | A first-generation cephalosporin, vancomycin, clindamycin, imipenem, amoxicillin-clavulanic acid, ticarcillin-clavulanic acid, ampicillin-sulbactam; a fluoroquinolone[b] |
| Methicillin-resistant | Vancomycin with or without gentamicin and/or rifampin | TMP-SMZ, minocycline |

TABLE 4-continued

ANTIBIOTICS OF CHOICE FOR COMMON PATHOGENS

| Pathogen | Antibiotic of First Choice[a] | Alternative Agents[a] |
|---|---|---|
| *Streptococci* | | |
| Group A, C, G | Penicillin | A cephalosporin[a], vancomycin, erythromycin; clarithromycin; azithromycin; clindamycin |
| Group B | Penicillin (or ampicillin) | A cephalosporin[a], vancomycin, or erythromycin |
| *Enterococcus* | | |
| Endocarditis or other serious infection | Penicillin (or ampicillin) with gentamicin | Vancomycin with gentamicin |
| Uncomplicated urinary tract infection | Ampicillin or amoxicillin | A fluoroquinolone, nitrofurantoin |
| Viridans group | Penicillin G (with or without gentamicin) | A cephalosporin[a], vancomycin |
| *S. bovis* | Penicillin G | A cephalosporin[a], vancomycin |
| *S. pneumoniae* | Penicillin G | A cephalosporin[a], erythromycin, chloramphenicol, vancomycin |
| Gram-negative cocci | | |
| *Neisseria gonorrhoeae* | Ceftriaxone | Spectinomycin, a fluoroquinolone, cefoxitin, cefixime, cefotaxime (see Appendix E) |
| *N. meningitidis* | Penicillin G | Third-generation cephalosporin, chloramphenicol |
| *Moraxella (Branhamella) catarrhalis* | TMP-SMZ | Amoxicillin-clavulanic acid; an erythromycin; clarithromycin azithromycin, cefuroxime, cefixime, third-generation cephalosporin, tetracycline |
| Gram-positive bacilli | | |
| *Clostridium perfringens* (and *Clostridium* sp.) | Penicillin G | Chloramphenicol, metronidazole, or clindamycin |
| *Listeria monocytogenes* | Ampicillin with or without gentamicin | TMP-SMZ |
| Gram-negative bacilli | | |
| *Acinetobacter* | Imipenem | Tobramycin, gentamicin, or amikacin, Usually with ticarcillin or piperacillin (or similar agent); TMP-SMZ |
| *Aeromonas hydrophila* | TMP-SMZ | Gentamicin, tobramycin; imipenem; a fluoroquinolone |
| *Bacteroides* | | |
| *Bacteroides* sp. (oropharyngeal) | Penicillin G | Clindamycin, cefoxitin, metronidazole, chloramphenicol, cefotetan, ampicillin-sulbactam |
| *B. fragilis* strains (gastrointestinal strains) | Metronidazole | Clindamycin; ampicillin-sulbactam; imipenem; cefoxitin[c]; cefotetan[c]; ticarcillin-clavulanic acid; piperacillin[c]; chloramphenicol; cefmetazole[c] |
| *Campylobacter fetus, jejuni* | A fluoroquinolone (adults) or an erythromycin | A tetracycline, gentamicin |
| *Enterobacter* sp. | Imipenem | An aminoglycoside and piperacillin or ticarcillin or mezlocillin; a third-generation cephalosporin[d]; TMP-SMZ; aztreonam; a fluoroquinolone |
| *Escherichia coli* | | |
| Uncomplicated urinary tract infection | TMP-SMZ | A cephalosporin or a fluoroquinolone |

TABLE 4-continued

ANTIBIOTICS OF CHOICE FOR COMMON PATHOGENS

| Pathogen | Antibiotic of First Choice[a] | Alternative Agents[a] |
|---|---|---|
| Recurrent or systemic infection | A cephalosporin[e] | Ampicillin with or without an aminoglycoside, TMP-SMZ, oral fluoroquinolones useful in recurrent infections, ampicillin-sulbactam, ticarcillin-clavulanic acid, aztreonam |
| *Haemophilus influenzae* (*coccobacillary*) | | |
| Life-threatening infections | Cefotaxime or ceftriaxone | Chloramphenicol; cefuroxime for pneumonia) |
| Upper respiratory infections and bronchitis | TMP-SMZ | Ampicillin or amoxicillin; cefuroxime; a sulfonamide with or without an erythromycin; cefuroxime-axetil; third-generation cephalosporin, amoxicillin-clavulanic acid, cefaclor, tetracycline; clarithromycin; azithromycin |
| *Klebsiella pneumoniae* | A cephalosporine[e] | An aminoglycoside, imipenem, TMP-SMZ, ticarcillin-clavulanic acid, ampicillin-sulbactam, aztreonam, a fluoroquinolone; amoxicillin-clavulanic acid |
| *Legionella* spp. | Erythromycin with rifampin | TMP-SMZ; clarithromycin; azithromycin; ciprofloxacin |
| *Pasteurella multocida* | Penicillin G | Tetracycline, cefuroxime, amoxicillin-clavulanic acid, ampicillin-sulbactam |
| *Proteus* sp. | Cefotaxime, ceftizoxime, or ceftriaxone[f] | An aminoglycoside; ticarcillin or piperacillin or mezlocillin; TMP-SMZ; amoxicillin-clavulanic acid; ticarcillin-clavulanic acid, ampicillin-sulbactam; a fluoroquinolone; aztreonam; imipenem |
| *Providencia stuartii* | Cefotaxime, ceftizoxime, or ceftriaxone[f] | Imipenem; an aminoglycoside often combined with ticarcillin or piperacillin or similar agent; ticarcillin-clavulanic acid; TMP-SMZ, a fluoroquinolone; aztreonam |
| *Pseudomonas aeruginosa* | | |
| (nonurinary tract infection) | Gentamicin or tobramycin or amikacin (combined with ticarcillin, piperacillin, etc. for serious infections) | An aminoglycoside and ceftazidime; imipenem, or aztreonam plus an aminoglycoside; ciprofloxacin Carbenicillin; ticarcillin, piperacillin, or mezlocillin; ceftazidime; imipenem; aztreonam; an aminoglycoside |
| (urinary tract infections) | Ciprofloxacin | |
| *Pseudomonas cepacia* | TMP-SMZ | Ceftazidime, chloramphenicol |
| *Salmonella typhi* | Ceftriaxone | Ampicillin, amoxicillin, TMP-SMZ, chloramphenicol; a fluoroquinolone |
| Other species | Cefotaxime or ceftriaxone | Ampicillin or amoxicillin, TMP-SMZ, chloramphenicol; a fluoroquinolone |
| *Serratia* | Cefotaxime, ceftizoxime, or ceftriaxone[f] | Gentamicin or amikacin; imipenem; TMP-SMZ; ticarcillin, piperacillin, or mezlocillin; aztreonam; a fluoroquinolone |

TABLE 4-continued

ANTIBIOTICS OF CHOICE FOR COMMON PATHOGENS

| Pathogen | Antibiotic of First Choice[a] | Alternative Agents[a] |
|---|---|---|
| Shigella | A fluoroquinolone | TMP-SMZ; ceftriaxone; ampicillin |
| Vibrio cholerae (chlorea) | A tetracycline | TMP-SMZ; a fluoroquinolone |
| Vibrio vulnificus | A tetracycline | Cefotaxime |
| Xanthomonas (Pseudomonas) maltophilia | TMP-SMZ | Minocycline, ceftazidime, a Fluoroquinolone |
| Yersinia enterocolitica | TMP-SMZ | A fluoroquinolone; an aminoglycoside; cefotaxime or ceftizoxime |
| Yersinia pestis (plague) | Streptomycin | A tetracycline; chloramphenicol; gentamicin |

Key:
TMP-SMZ = trimethoprim-sulfamethoxazole.
[a]Choice presumes susceptibility studies indicate that the pathogen is susceptible to the agent.
[b]The experience with fluoroquinolone use in *staphylococcal* infections is relatively limited. The fluoroquinolones should be used only in adults.
[c]UP to 15–20% of strains may be resistant.
[d]*Enterobacter* spp. may develop resistance to the cephalosporins.
[e]Specific choice will depend on susceptibility studies. Third-generation cephalosporins may be exquisitely active against many Gram-negative bacilli (e.g., *E. coli*, *Klebsiella* sp.). In some geographic areas, 20–25% of community-acquired *E. coli* infections may be resistant to ampicillin (amoxicillin).
[f]In severely ill patients, this is often combined with an aminoglycoside while awaiting susceptibility data.

TABLE 5

COMMON PATHOGENS IN FOCAL INFECTIONS

| Presumed location of Infection | Common pathogens | Gram stain Characteristics of exudate-if available |
|---|---|---|
| Urinary tract infections | Community-acquired: *Escherichia coli* | GNB |
| | | GNB |
| | Recurrent or nosocomial: *E. coli*: *Klebsiella*, *Proteus*, *Pseudomonas* sp. *Enterococci* | GPC |
| Intravenous catheter phlebitis and/or sepsis | *Staphylococcus aureus* or *S. epidermidis* *Klebsiella*, *Enterobacter*, *Pseudomonas* sp. | GPC GNB Budding yeast; |
| Peripheral catheter Hyperalimentation line | *Candida* sp., *S. aureus*, *S. epidermidis*, enterococci *Klebsiella*, *Enterobacter* sp., etc. | GPC GNB |
| Arteriovenous shunt | *S. aureus*, *S. epidermidis* | GPC |
| Septic bursitis | *S. aureus* | GPC |
| Biliary tract | *E. coli*, *Klebsiella* sp., and enterococci; *Bacteroides fragilis* (in elderly patients), *Clostridia* sp. | |
| Intra-abdominal abscess, peritonitis, or large bowel perforation; diverticulitis[a] | *E. coli* *B. fragilis* *Klebsiella* sp. (*Enterococci*) | GNB GNB (thin, irregularly stained) GNB GPC |
| Burn wounds | Early: *S. aureus*, streptococci Later: Gram-negative bacilli, fungi | |
| Cellulitis, wound and soft tissue infections | *S. aureus* Streptococci *Clostridium* sp. | GPC GPC GPB |
| Meningitis | | |
| Pneumonia | | |
| Pelvic abscess, postabortal or postpartal | *Anaerobic streptococci* *B. fragilis* *Clostridium* sp. *E. coli* *Enterococci* | GPC GNB (thin, irregularly stained) GPB GNB GPC |

TABLE 5-continued

COMMON PATHOGENS IN FOCAL INFECTIONS

| Presumed location of Infection | Common pathogens | Gram stain Characteristics of exudate-if available |
| --- | --- | --- |
| Septic arthritis | S. aureus | GPC |
| | Haemophilus influenzae (in children younger than 6 yr) | GNC |
| | Group B streptococci (in neonates) | GPC |
| | Gram-negative organisms[b] | GNB |
| Acute osteomyelitis | S. aureus | GPC |
| | H. influenzae (in children younger than 6 yr) | GNC |
| | Group B streptococci (in neonates) | GPC |
| | Gram-negative organisms[b] | GNB |

Key:
GNB = Gram-negative bacilli;
GPC = Gram-positive cocci;
GPB = Gram-positive bacilli;
GNC = Gram-negative *coccobacilli*.
[a]The precise role of *enterococci* in intra-abdominal infections is unclear. In mild to moderate infections, it may not be necessary to provide antibiotic activity against *enterococci*.
[b]In high-risk patients (e.g., immunocompromised, elderly, IV drug abusers, diabetics, debilitated patients).

In other embodiments, the present invention will provide treatments for non-bacterial microbial infections. Virus infection relies on CKII and RPL41 is able to inhibit CKII activity. Therefore, RPL41 should interfere with viral infections. Viral infections include, but are not limited to, those caused by retrovirus, lentivirus, rhabdovirus (rabies virus), paramyxovirus (parainfluenza virus, measles virus, mumps virus, canine distemper virus, respiratory syncytial virus), bunyavirus (hantavirus, nairovirus, phlebovirus, bunyavirus), arenavirus, rotavirus, picornavirus (coxsackie virus, polio virus, rhinovirus), influenza virus, herpesvirus (HSV-1, HSV-2, CMV, EBV, PRV), coronavirus, picornavirus, reovirus, hepadnavirus and parvovirus. Antiviral drugs that may be used in combination with RPL41 related agents in accordance with the present invention include reverse trasncriptase inhibitors (abacavir, didanosine, lamivudine, stavudine, zidovudine, efavirenz, nevirapine), protease inhibitors (indinavir, ritonavir, liponavir, nelfinavir, saquinavir), nucleotide analogs (gancyclovir, acyclovir, valacyclovir), kutapressin, inoprinosine, foscarnet, and interferons α and β.

Various molds/fungi that can be treated by the methods of the invention include those of the *Aspergillus* species, the *Fusarium* species, and/or the *Scedosporium* species. Some non-limiting examples of moulds of the *Aspergillus* species include *Aspergillus fumigatus, Aspergillus flavus, Aspergillus terreus, Aspergillus vesicularis, Aspergillus nidulans*, or *Aspergillus niger*. Non-limiting examples of moulds of the *Fusarium* species include *Fusarium solani* and those of the *Scedosporium* species include *Scedosporium prolificans*. Various fungicides that may be used in conjunction with the present invention include 2-aminobutane; 2-anilino4-methyl-6-cyclopropl-pyrimidine; 2',6'-dibromo-2-methyl-4'-trifluoromethoxy-4'-trifluoro-methyl-1,3-thiazole-5-carboxamide; 2,6-dichloro-N-(4-trifluoromethylbenzyl)-benzamide; (E)-2-methoxyirnino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metirarn, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procyrnidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

D. Combined Cancer Therapy

In order to increase the effectiveness of RPL41 peptides or mimics or analogs thereof, it may be desirable to combine these compositions with another agent effective in the treatment of cancer. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, overcoming drug or multidrug resistance, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

The RPL41 peptide or mimic or analog may precede, be co-current with and/or follow the other agent(s) by intervals ranging from minutes to weeks. In embodiments where the RPL41 peptide or mimic or analog, and other agent(s) are applied separately to a cell, tissue or organism, one would generally ensure that a significant period of time did not expire between the time of each delivery, such that the peptide and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the RPL41 peptide or mimic or analog. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 18 hours, about 24 hours, about 36 hours, about 48 hours, about 3 days, about 4 days, about 5 days, about 6 days, about 7 days, about 8 days, about 9 days, about 10 days, about 11 days, about 12 days, about 13 days, about 14 days, about 21 days, about 4 weeks, about 5 weeks, about 6 weeks, about 7 week or about 8 weeks or more, and any range derivable therein, prior to and/or after administering the RPL41 peptide or mimic or analog.

Various combination regimens of the RPL41 treatment and one or more other anti-cancer agents may be employed. Non-limiting examples of such combinations are shown below, wherein a RPL41 composition is "A" and the other anti-cancer agent is "B":

```
A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A
```

Administration of the RPL41 compositon to a cell, tissue or organism may follow general protocols for the administration of pharmaceuticals, taking into account the toxicity, if any. It is expected that the treatment cycles would be repeated as necessary. In particular embodiments, it is contemplated that various additional agents may be applied in any combination with the present invention.

i. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, *cholera* toxin, *pertussis* toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

iv. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Gene Therapy

In accordance with the present invention, one may combine Ad-TRAIL therapy with various other gene therapies. Therapeutic polypeptides are described below.

Tumor Suppressors. The tumor suppressor oncogenes function to inhibit excessive cellular proliferation. The inactivation of these genes destroys their inhibitory activity, resulting in unregulated proliferation. The tumor suppressors p53, Rb and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with viral proteins such as large-T antigen and E1B. The protein is found in normal tissues and cells, but at concentrations which are minute by comparison with transformed cells or tumor tissue.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Inducers of Apoptosis. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $BCl_{XL}$, $Bcl_W$, $Bcl_S$, Mcl-1, Al, Bfl-1) or counteract Bcl-2 function and promote cell death (e.g., Bax, Bak, Bik, Bim, Bid, Bad, Harakiri).

Inducers of Cellular Proliferation. The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that antisense or ribozyme construct directed to a particular inducer of cellular proliferation is used to prevent expression of the inducer of cellular proliferation.

The proteins FMS, ErbA, ErbB and Neu are growth factor receptors. Mutations to these receptors result in loss of regulatable function. For example, a point mutation affecting the transmembrane domain of the Neu receptor protein results in the Neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc also are proteins that directly exert their effects on nuclear functions as transcription factors. An extensive list of oncogenes that could be the targets for antisense therapy is present below.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymidine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

Particular oncogenes that are targets for antisense constructs are ras, myc, neu, raf, erb, src, fms, jun, trk, ret, hst, gsp, bcl-2 and abl. Also contemplated to be useful will be anti-apoptotic genes and angiogenesis promoters.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). Ribozyme catalysis has primarily been observed as part of sequence-specific cleavage/ligation reactions involving nucleic acids (Joyce, 1989). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme. Targets for this embodiment will include angiogenic genes such as VEGFs and angiopoietins as well as the oncogenes (e.g., ras, myc, neu, raf, erb, src, fms, jun, trk, ret, hst, gsp, bcl-2, EGFR, grb2 and abl).

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity. (Fire et al., 1998; Grishok et al., 2000; Ketting et al., 1999; Montgomery et al., 1998; Sharp et al., 2000; Tabara et al., 1999). Activation of these mechanisms targets mature, dsRNA-complementary MRNA for destruction. RNAi offers major experimental advantages for study of gene function. These advantages include a very high specificity, ease of movement across cell membranes, and prolonged down-regulation of the targeted gene. (Fire et al., 1998; Grishok et al., 2000; Ketting et al., 1999; Montgomery et al., 1998; Sharp, 1999; Sharp et al., 2000; Tabara et al., 1999).

siRNAs must be designed so that they are specific and effective in suppressing the expression of the genes of interest. Methods of selecting the target sequences, i.e. those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above. (Montgomery et al., 1998).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25–100 nM. This had been demonstrated by Elbashir et. al. (2001) wherein concentrations of about 100 nM achieved effective suppression of expression in mammalian cells. siRNAs have been most effective in mammalian cell culture at about 100 nM. In several instances, however, lower concentrations of chemically synthesized siRNA have been used (Caplen et. al., 2000; Elbashir et. al., 2001). WO 99/32619 and WO 01/68836 suggest that RNA for use in siRNA may be chemically or enzymatically synthesized. Both of these texts are incorporated herein in their entirety by reference. Similarly, WO 00/44914, incorporated herein by reference, suggests that single strands of RNA can be produced enzymatically or by partial/total organic synthesis. WO 01/36646, incorporated herein by reference, places no limitation upon the manner in which the siRNA is synthesized, providing that the RNA may be synthesized in vitro or in vivo, using manual and/or automated procedures.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which are equipped at each end with a promoter sequence. The templates are preferably attached to a solid surface. After transcription with RNA polymerase, the resulting dsRNA fragments may be used for detecting and/or assaying nucleic acid target sequences.

Cytokines. Another class of genes that is contemplated to be inserted into the adenoviral vectors of the present invention include interleukins and cytokines. Interleukin 1 (IL-1), IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, GM-CSF, G-CSF, M-CSF and tumor necrosis factor.

Toxins. Various toxins are also contemplated to be useful as part of the expression vectors of the present invention, these toxins include bacterial toxins such as ricin A-chain (Burbage, 1997), diphtheria toxin A (Massuda et al., 1997; Lidor et al., 1997), pertussis toxin A subunit, E. coli enterotoxin toxin A subunit, cholera toxin A subunit and pseudomonas toxin c-terminal. It has been demonstrated that transfection of a plasmid containing the fusion protein regulatable diphtheria toxin A chain gene was cytotoxic for cancer cells. Thus, gene transfer of regulated toxin genes might also be applied to the treatment of cancers (Massuda et al., 1997).

Single Chain Antibodies. In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules are contemplated, such as oncogenes, growth factors, hormones, enzymes, transcription factors or receptors. Also contemplated are secreted antibodies, targeted to serum, against angiogenic factors (VEGF/VSP; βFGF; αFGF) and endothelial antigens necessary for angiogenesis (i.e., V3 integrin). Specifically contemplated are growth factors such as transforming growth factor and platelet derived growth factor.

Transcription Factors and Regulators. Another class of genes that can be applied in an advantageous combination are transcription factors. Examples include C/EBPα, IκB, NFκB, Par-4 and C/EBPα.

Cell Cycle Regulators. Cell cycle regulators provide possible advantages, when combined with other genes. An example of a regulator that serves to inhibit cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$, which has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Okamoto et al., 1994; Nobori et al., 1995; Orlow et al., 1994). Restoration of wild-type p16$^{INK4}$ function by transfection with a plasmid expression vector reduced colony formation by some human cancer cell lines (Okamoto, 1994).

Other such cell cycle regulators include p27, p21, p57, p18, p73, p19, p15, E2F-1, E2F-2, E2F-3, p107, p130 and E2F-4. Other cell cycle regulators include anti-angiogenic proteins, such as soluble Flt1 (dominant negative soluble VEGF receptor), soluble Wnt receptors, soluble Tie2/Tek receptor, soluble hemopexin domain of matrix metalloprotease 2 and soluble receptors of other angiogenic cytokines (e.g. VEGFR1/KDR, VEGFR3/Flt4, both VEGF receptors).

Chemokines. Genes that code for chemokines also may be used in the present invention. Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Such chemokines include RANTES, MCAF, MIP1-alpha, MIP1-Beta, and IP-10. The skilled artisan will recognize that certain cytokines are also known to have chemoattractant effects and could also be classified under the term chemokines.

vi. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

E. Pharmaceutical Formulations

Pharmaceutical formulations of the present invention comprise an effective amount of a RPL41 agent dissolved or dispersed in a pharmaceutically acceptable carrier. The phrases "pharmaceutical or pharmacologically acceptable" refer to compositions that do not produce an adverse, allergic or other untoward reaction when administered to an animal, such as, for example, a human, as appropriate. The preparation of such pharmaceutical compositions are known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

The pharmaceuticals of the present invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The pharmaceuticals may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required; followed by filtered sterilization.

Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

7. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

RPL41 Tumor Suppressor Activity

1. Materials and Methods

Functional screening of transforming genes. Total RNAs from primary tumors were isolated with TriPure Isolation Reagents (Invitrogen). mRNAs were isolated with a Oligotex MRNA mini-kit (Qiagen). cDNAs were synthesized with a SMART PCR cDNA synthesis kit (Clontech). For first-strand cDNA synthesis, 1 µg of mRNA was reverse transcribed with a PowerScript reverse transcriptase, an oligo d(T) 3' adaptor primer, and a SMART II A oligonucleotide containing a terminal stretch of G residues that serve as an extended template for reverse transcription (5' adaptor). First-strand cDNAs were amplified with 10 cycles of PCR using the adaptor primers. PCR products were TA cloned into pcDNA3.1/V5-His TOPO expression vector (Invitrogene). Plasmid DNA was transfected into NIH 3T3 cells with Lipofectamine 2000 reagents (Invitrogen). Cells were selected in the presence of neomycin for 3 weeks before proceeding to a soft-agar assay. Transfected cells ($2 \times 10^5$) were suspended in 15 ml of soft agar equilibrated at 40° C. (0.35% Bactoagar in RPMI 1640 with 10% FCS), plated on 20 ml of solidified agar (0.5% Bactoagar in RPMI 1640 with 10% FCS) in a P-150 culture dish. Six P-150 soft-agar plates, including three for breast cancer cDNAs and three for prostate cancer cDNAs, were used for this study. Soft-agar plates were cultured at 37° C. in 5% $CO_2$ for 3 weeks. For the negative control, NIH3T3 cells were transfected with empty vector, selected in the presence of neomycin, and seeded in a P-35 soft-agar plate. Transformed colonies were picked up under a phase microscope with 1000-µl pipette tips with their tips cut off. Colonies were disaggregated with trypsin and expanded in liquid culture. Cells were harvested and DNAs were isolated. Tumor genes were rescued by PCR with adaptor primers (from the SMART PCR cDNA synthesis kit). PCR products were sequenced with a primer derived from the 5' daptor sequence (5'-CGCAGAG-TACGCGGG-3' (SEQ ID NO:4)). The expression orientation of each candidate cancer gene was determined by PCR with a forward primer derived from a vector sequence upstream of the cloning site (T7 promoter primer) and one of the two gene-specific reverse primers: one complementary to the sense strand of the gene and the other complementary to the antisense strand of the gene.

Mutation analysis of RPL41. PCR was performed to amplify a 914-bp genomic region covering the entire RPL41 coding sequence with a forward primer (5'-CCATAGA-CATCTGACCTCGGCAC (SEQ ID NO:5)) and reverse primer (5'-GTCCCACAACTTGTAGCCAGCATC (SEQ ID NO:6)). PCR conditions were as follows: initial denaturation at 95° C. for 1 min followed by 30 cycles of denaturation at 95° C. for 5 sec, annealing at 60° C. for 30 sec, and extension at 72° C. for 1 min. An aliquot of PCR products was analyzed in 0.8% agarose gel. The remaining PCR products were purified with a PCR purification kit (Qiagen) and sequenced with an ABI 373A machine.

Fluorescence in situ hybridization (FISH). Cells were cultured in the presence of Colcemid overnight, harvested by trypsin treatment, incubated with hypotonic solution, and fixed in methanol and acetic acid (3:1). BAC (CTD-2560J16) clone was obtained from the BACPAC Resource Center (BPRC) at Children's Hospital Oakland Research Institute in Oakland, Calif. BAC DNA was isolated and biotin labeled by random octamer priming (BioPrime DNA Lebeling System, Invitrogen). Hybridization, signal detection and image analysis were as described previously (Xiao et al. 1995).

CK2 Kinase Assay. CK2 kinase assay was performed using a synthetic peptide substrate, RRRDDDSDDD (SEQ ID NO:7), as described previously (Litchfield et al., 1990). In brief, 100 µg crude cell lysates were incubated with 200 µM peptide substrate in 20 mM Tris-Cl, pH 7.5, 60 mM NaCl, 10 mM $MgCl_2$, 1 mM DTT, and 100 µM [$\gamma$-$^{32}$P]ATP for 10 min at 30° C. An aliquot of the reaction was spotted on P81 phosphocellulose paper, washed extensively with 0.75% phosphoric acid, washed once with acetone, and quantified using a scintillation counter.

2. Results

Figure 2:
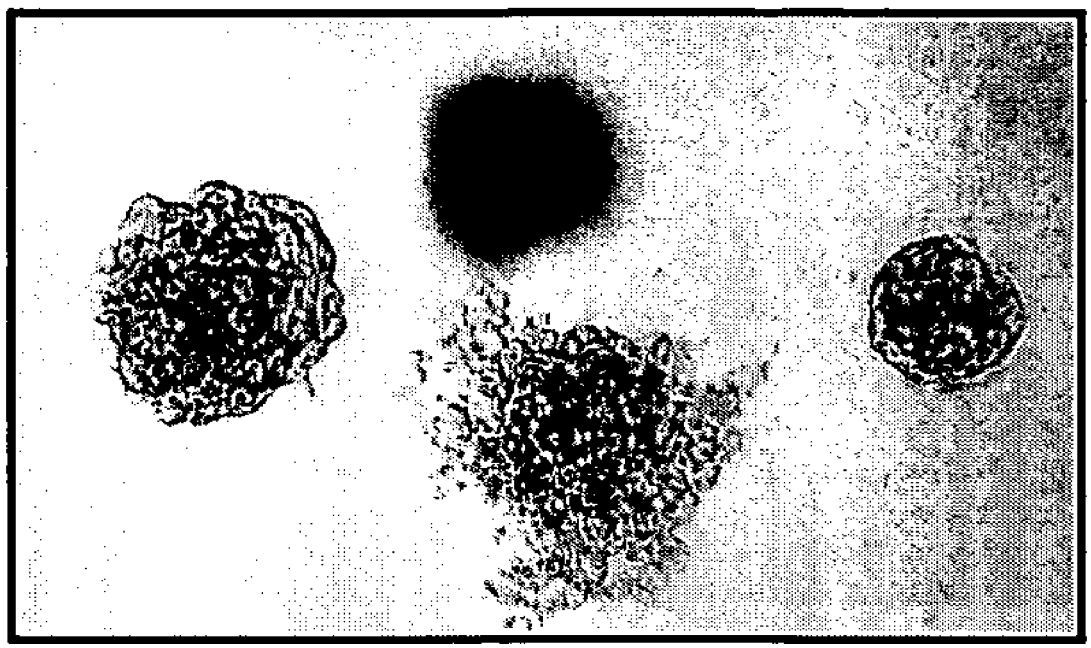
FIG. 2—NIH3T3 cells expressing tumor genes formed colonies in soft-agar culture. The morphology of colonies ranged from rounded with a smooth boundary to branch-like with no clear boundary, presumably due to different functions of the expressed genes.

Identification of RPL41 as a candidate tumor suppressor gene. The inventor designed a functional screening approach to identify genes capable of inducing cell transformation (FIG. 1). Genes from primary tumors were expressed in both sense and antisense orientation in non-neoplastic NIH3T3 cells. Cells were cultured in soft-agar plates. Transformed 3T3 cells were identified by their capabilities for anchorage-independent growth. Tumor genes were rescued and sequenced. Genes expressed in sense orientation were considered candidate oncogenes, and those expressed in antisense orientation, which should down-regulate the expression of their counterpart in NIH3T3 cells, were considered candidate tumor suppressor genes. The inventor performed two parallel studies using RNAs from either a mixture of four primary breast cancers or a mixture of three primary prostate cancers. NIH3T3 cells transfected with tumor cDNAs were selected for neomycin resistance for 3 weeks. During this period, a few foci of piled-up cells were observed among cells expressing tumor genes but not among control cells expressing vector only. Transfected cells were then seeded in soft-agar culture plates. In 2 weeks, many colonies were formed from cells transfected with tumor cDNAs, but none were formed from control cells. The morphology of the transformed colonies varied, presumably due to different functions of individual genes expressed in those colonies (FIG. 2).

Fifty-six colonies from cells expressing breast cancer cDNAs and 64 colonies from cells expressing prostate cancer cDNAs were picked up under a phase microscope with 1000-μl pipette tips with their tips cut off. Colonies were disaggregated with trypsin and expanded in liquid culture. Cells were harvested and tumor genes were rescued by PCR with adaptor primers. Most of the colonies contained one tumor gene or one tumor gene fragment. A total of ten genes, including three genes in sense orientation and seven genes in antisense orientation, were discovered. Two known tumor suppressor genes, TSG101 and MM-1 (encoding a negative regulator for a c-Myc), were among the seven genes identified in antisense orientation. Other candidate tumor suppressor genes included RPL41, UTRN, SMARCF1 (matrix-associated, actin-dependent regulator of chromatin, subfamily f, member 1), and two novel genes. Six independent transforming colonies contained the antisense transcript of a single gene encoding RPL41, which is the smallest and most basic component of the ribosome, with only 25 amino acids consisting of 68% of basic amino acid residues (Klaudiny et al. 1992; Suzuki et al. 1990).

To evaluate potential RPL41 mutation in tumors, PCR was performed to amplify a 914-bp genomic region covering the entire RPL41 coding sequence. PCR products were directly sequenced. No mutations or homozygous deletions of RPL41 were identified in 24 tumor cell lines (ATCC) studied. FISH analysis with a BAC clone containing RPL41 (CTD-2560J16) and a chromosome 12 centromere control probe; however, showed RPL41 allelic reduction in 12 of 24 tumor cell lines, including 4 of 7 breast cancers, 2 of 5 prostate cancers, 4 of 4 lung cancers, 1 of 4 acute myeloid leukemias, 1 of 1 malignant melanoma, 0 of 1 acute lymphoblastic leukemia, 0 of 1 chronic myeloid leukemia, and 0 of 1 colon cancer (FIGS. 3A–D). Previous studies of zebrafish with tumors suggested that the essential ribosomal protein genes could function as haploinsufficient tumor suppressors (Amsterdam et al. 2004). The observation of RPL41 allelic reduction in tumors could suggest a similar haploinsufficient tumor suppressor mechanism.

Inhibition of tumor cell growth by RPL41. The tumor suppressor function of RPL41 was evaluated by expressing an RPL41 construct containing the entire coding region of RPL41 in three tumor cell lines, including a breast cancer (MCF7), a prostate cancer (HTB81), and a lung cancer (CRL5803). In a soft agar assay, the expression of RPL41 in all three tumor cell lines inhibited their colony formation in soft agar cultures (FIGS. 4A–B). A RPL41/GFP fusion construct was also assembled and expressed in five tumor cell lines (malignant melanoma HTB72, prostate cancer CRL1435, lung cancer CRL5800, colon cancer HCT116, breast cancer MCF7). As expected, RPL41/GFP fusion was most located in nucleolus and cytoplasm of cells. In all five cell lines, most tumor cells expressing RPL41/GFP died three days after transfection. No such selection against the control cells expressing GFP only was observed (FIGS. 5A–C).

Tumorigenesis of RPL41-transfected or vector-transfected breast cancer MCF7 cells and prostate cancer HTB81 cells in athymic CD-1 nude mice was studied by injecting $2 \times 10^6$ tumor cells subcutaneously into each mouse. Three weeks later, all mice injected with vector-transfected tumor cells (four mice with MCF-7 and four mice with HTB81) developed tumors. None of the four athymic mice injected with RPL41-transfected MCF7 cells and one of the four athymic mice injected with RPL41-transfected HTB81 cells formed tumors.

The inventor next studied the effect of a synthetic RPL41 peptide on tumor cell growth. As a ribosomal protein, RPL41 presumably exerts its function in the cytoplasm and nucleolus. Therefore, a prerequisite for the function of synthetic RPL41 is permeability inside cells. RPL41 encodes a very basic peptide that contains 10 arginine and 7 lysine residues with a pI at 12.96. Previous studies showed that arginine-rich peptides were able to permeate cell membranes and that peptides with more than 7 arginine residues had the highest internalization efficiency (Futaki et al., 2003). To study the possibility of a cell-permeable RPL41, a synthetic RPL41 conjugated with FITC at its N terminal was incubated with cells seeded in a chamber slide for 15 minutes and then washed living cells and observed them under a fluorescence microscope. RPL41 was found predominantly in the nucleolus of cells, and granular fluorescence was found in the cytoplasm (FIG. 6A), suggesting that RPL41 peptide was able to permeate through both the plasma membrane and nuclear pore. The inventor then studied the effect of the synthetic RPL41 on tumor cell growth on 24 tumor cell lines of various tissue types (ATCC). Tumor cells were cultured in 96-well plates with 10% fetal bovine serum (FBS) in the presence of increasing amounts of the RPL41 peptide or vehicle control. Cells were counted by trypan blue exclusion after 48 hours of culture. All 24 tumor cell lines showed significant dose-dependent growth inhibition. Most tumor cells were killed with 8.2 μM synthetic RPL41 (FIG. 6B).

The effect of the synthetic RPL41 on normal cell growth was studied by incubating RPL41 with human primary fibroblasts, human primary epithelial cells, and human bone marrow cells (human cells were obtained with IRB approval from the Cytogenetics Laboratory at Brigham and Women's Hospital from discarded patient material). Normal cells were much more resistant than tumor cells to RPL41. The inventor consistently found that a greater than five-fold higher concentration of RPL41 was needed to achieve the same cell inhibition effect in normal cells achieved in cancer cells (FIG. 6A). The preferential selection of tumor cells by RPL41 was also demonstrated in an experiment in which a mixture of tumor epithelial cells (CRL5803) and normal fibroblasts was cultured in the presence of 8.2 μM RPL41 or vehicle control. After one week of culture, only fibroblasts were left growing in the culture with RPL41 whereas a mixture of tumor epithelial cells and normal fibroblasts were growing in the control culture, as confirmed by FISH analysis of nuclei with a probe to chromosome 5 centromere sequences, which showed four or five copies of chromosome 5 in tumor cells and disomy 5 in normal cells (data not shown)

Interestingly, a control scrambled RPL41 peptide (NH2-KARMRMKRKLRKRMRKRQRSRKWKR-OH (SEQ ID NO:8); also showed some inhibition effect on tumor cell growth. At a similar concentration, the scrambled RPL41 peptide had approximately 20% inhibition effect on tumor cell growth, compared to that of RPL41 peptide. The inhibition effects on tumor cell growth, for both scrambled and RPL41 peptides, were completely abolished when the peptides were pre-treated with proteases (DIGEST-ALL, Zymed). Another control peptide (MLISSGLKDGIRSGI (SEQ ID NO:9); unrelated to RPL41 and with a pI at 8.5, had no effect on tumor cell growth even at a concentration ten times higher than that of RPL41. Because RPL41 is such a basic protein, it is possible that some of its functions are contributed by its unique amino acids composition. RPL41 interacts with CK2, which will be discussed later, to induce autophagic cell death. CK2 contains clusters of acidic residues that are known to interact with polybasic compounds. It is quite possible that the scrambled RPL41 peptide also interact, albeit to a lesser degree, with CK2.

Figure 9:
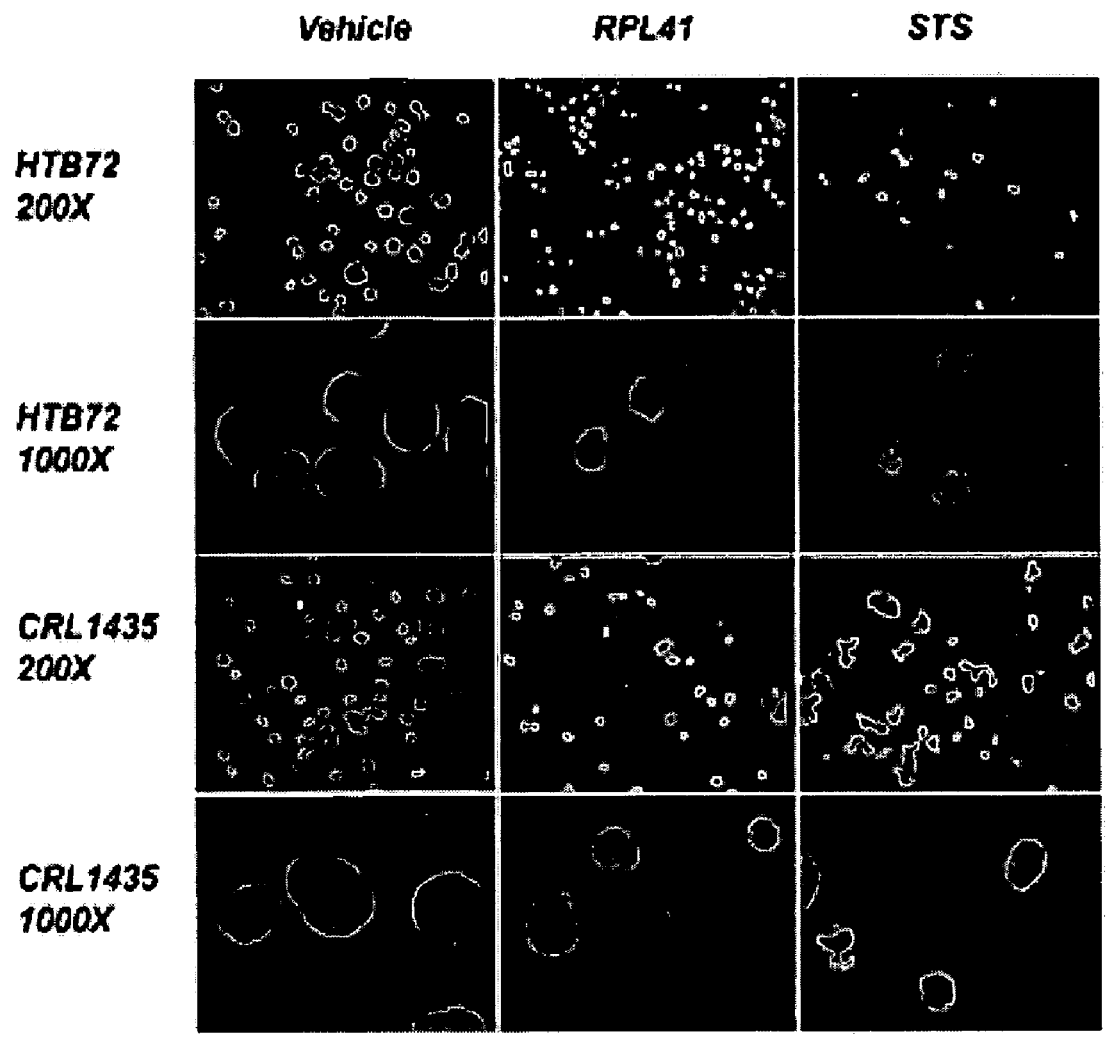
FIG. 9—Nuclear morphology changes in tumor cells treated with RPL41. Tumor cells (CRL1435 and HTB72) were treated with RPL41 peptide (6.7 µM), vehicle control or a known apoptosis inducer staurosporine (STS; 2 µM) overnight, followed by nuclear staining with Hoechst 33342.

Autophagic cell death induced by RPL41. Tumor cells treated with RPL41 showed dramatic morphologic changes including cell rounding, cell shrinkage, and massive membrane blebbing (FIGS. 7A–J). Terminal deoxynucleotidyl transferase-mediated nick end labeling (TUNEL) assay showed that most cells treated with RPL41 were TUNEL positive (FIGS. 8A–D). No DNA fragmentation, however, was observed by DNA ladder assays. Hoechst 33342 staining of cells treated with RPL41 showed that nucleus was shrunk and the boundary of nucleus was fuzzy. No nuclear fragmentation and pyknosis of nucleus were seen (FIG. 9). The inventor then studied the mitochondrial transmembrane potential ($\Delta\psi_m$) in RPL41-treated tumor cells by incubating with a fluorescent cation dye JC-1. As showed in FIGS. 8A–B, most cells treated with RPL41 were green cells without red signals, consistent with dissipation of $\Delta\psi_m$.

Figure 10:
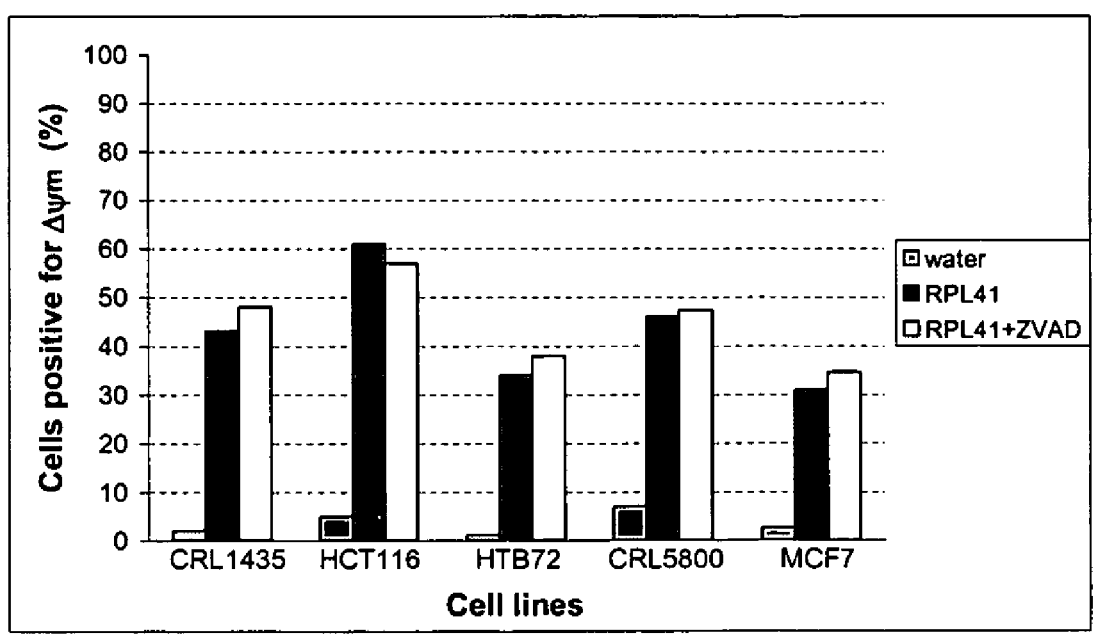
FIG. 10—RPL41 induced cell death is caspase independent. Five tumor cell lines, including malignant melanoma HTB72, prostate cancer CRL1435, lung cancer CRL5800, colon cancer HCT116, breast cancer MCF7, were cultured in chamber slides, treated with RPL41 peptide (6.7 µM) alone, RPL41 peptide and Z-VAD.fmk (50 µM), or vehicle control for 8 hours, and subjected to mitochondrial transmembrane potential ($\Delta\psi_m$) assay.

Western blot analysis was performed to study the potential roles of caspases in RPL41 induced cell death. No obvious cleavages of caspases 3, 6, 7 and 9 were observed in tumor cells treated with RPL41 for 1, 6 and 24 hours. Two main targets of caspase cleavages, PARP and DFF45/DFF35, remained intact in cells treated with RPL41 (data not shown). The cell death induced by RPL41, therefore, is likely to be caspase-independent. A broad-spectrum caspase inhibitor z-VAD.fmk was also incubated with five tumor cell lines, in the presence of RPL41, to determine whether the inhibition of caspases will attenuate RPL41 induced cell death. Both morphologic assessment under phase microscope and $\Delta\psi_m$ assays showed that z-VAD.fmk failed to suppress the RPL41 induced cell death in all five cell lines studied, consistent with caspase-independent cell death (FIG. 10).

Autophagic cell death is a caspase-independent event characterized by the formation of double or multiple membrane autophagic vesicles that engulf bulk cytoplasm and cytoplasmic organelles. Two signaling pathways, involving microtubule-associated protein 1 light chain 3(MAP1LC3) and death-associated protein kinase (DAPk), are known to play important roles in autophagic cell death. MAP1LC3 has two isoforms: LC3-I and LC3-II; both are cleaved products from proLC3. LC3-II, but not LC3-I and proLC3, binds to a lipid molecule phosphatidylethanolamine (PE) and starts the formation of autophagic vesicles. In cells doomed to autophagic cell death, both proLC3 and LC3-I are converted to LC3-II. The conversion of proLC3 and LC3-I to LC2-II has been suggested as a specific marker for the activation of autophagic signaling. Western blotting analysis on tumor cells treated with RPL41 showed decreased proLC3 and LC3-I and increased LC3-II, consistent with autophagic cell death (FIG. 11A).

DAPk is a $Ca^{2+}$/calmodulin-regulated ser/Thr kinase. Although the molecular mechanisms are not clear at present, DAPk activation leads to membrane blebbing and autophagic cell death. DAPk has a unique intrinsic negative regulation mechanism, which is achieved by the autophosphrylation of $Ser^{308}$. Up on death stimulus, DAPk is activated by the dephosphorylation of $Ser^{308}$. Western blotting analysis with an antibody specific to $Ser^{308}$ phophorylated DAPk showed DAPk was dephosphorylated when tumor cells were treated with RPL41, consistent with the activation of DAPk and induction of autophagic cell death (FIG. 11B).

RPL41 inhibited protein synthesis via inhibition of CK2 activity. Several studies showed autophagic cell death can be induced by the inhibition of translation initiation. To study whether an excess RPL41 interfere with protein synthesis, cells were quiesced in culture medium with 0.5% FBS overnight before switching to culture medium with 20% FBS containing [$^{35}$S]methionine, in the presence or absence of RPL41. As shown in FIG. 12A, exogenous RPL41 significantly inhibited protein synthesis. An in vitro transcription and translation assay showed that RPL41 did not affect the transcription while exerting powerful inhibition of protein synthesis, consistent with its action at the translational level (data not shown).

CK2 plays an important role in translation initiation by phosphorylating eIF2B, eIF2beta and eIF5. The association between CK2 and malignant transformation has been long recognized. For example, enhanced CK2 activity has been observed in many types of tumors (Ahmed et al., 2000). In nude mice, overexpression of the CK2α subunit leads to tumor formation (Seldin and Leder, 1995). On the other hand, modest downregulation of CK2 activity by 40% in tumor cells treated with antisense CK2α oligonucleotides resulted in dramatic inhibition of cell growth and in the induction of apoptosis (Faust et al., 2000). RPL41 is known to be associated with the β subunit of casein kinase 2 (CK2) (Lee et al., 1997). To study whether the administration of RPL41 affects CK2 activity, tumor cells were cultured in the presence of increasing amounts of RPL41 peptide or vehicle control for 30 minutes, harvested the cells, and then performed a CK2 kinase assay with a CK2-specific substrate (RRRDDDSDDD (SEQ ID NO:7). A dose-dependent inhibition of CK2 activity was observed, with a 30% decrease in CK2 activity at 0.7 μM RPL41, a 45% decrease at 3.7 μM RPL41, and a 47% decrease at 8.2 μM RPL41 (FIG. 12B). To study whether RPL41 inhibits tumor cell growth via regulating CK2 activity, a siRNA specific to CK2 β regulatory subunit was transfected into tumor cells. Knock-down of CK2β regulatory subunit did not affect tumor cell growth. These cells, however, were completely resistant to the administration of RPL41.

Inhibition of mouse tumors by RPL4. The anti-tumor effect of synthetic RPL41 on a mouse tumor model was studied. Athymic mice were injected subcutaneously with $2\times10^7$ colon cancer cells (HCT116). Tumors were allowed to grow for five days (to 0.18 cm$^3$). Mice were then treated intraperitoneally with 0.5 ml of control saline solution or RPL41 (7.5 mg/kg per day in 0.5 ml of saline solution) for 20 days. In saline-treated mice, the mean tumor size reached 2.5 cm$^3$, whereas in RPL41-treated mice, the mean tumor size reached 0.67 cm$^3$. Therefore, RPL41 treatment inhibited tumor growth by 73% (FIG. 13A). Intra-tumor injection of RPL41 (30 mg/kg/day for 2 days) was also performed on a mouse tumor derived from lung cancer cells (CRL5803). Four weeks after treatment, virtually no tumor growth was observed, while the volume of a control tumor treated with saline increased fivefold (FIG. 13B). It should be noted that RPL41 peptide did not appear to be toxic to the mice because no weight loss or alter of activity was observed in mice treated with RPL41 at the end of the experiment.

3. Summary

In summary, the inventor confirmed a tumor suppressor role for RPL41 by using different approaches and showed that RPL41 induced autophagic cell death via down-regulating CK2 activity. The elevated CK2 activity in tumor cells versus the activity in normal cells may explain the preferential selection of the synthetic RPL41 against tumor cells. The clinical prospect of RPL41 as a targeted anti-tumor reagent is promising. These studies show that a synthetic RPL41 can penetrate both the plasma membrane and nuclear pore, suggesting intracellular bioavailability. Administration of synthetic RPL41 is not likely to be immunogenic, since RPL41 is universally present in normal cells. The inventor observed that several types of normal cells are much more tolerant of synthetic RPL41 than are tumor cells, suggesting that RPL41 portends a low risk of cytotoxic side effects. The expected anti-tumor activity of RPL41 is broad because the first 24 tumor cell lines studied—including breast cancer, prostate cancer, lung cancer, colon cancer, malignant melanoma, and leukemia—all responded to RPL41.

Example 2

RPL41 Anti-Microbial Activity

The inventor also studied the antibacterial potential of RPL41. Insects, amphipathic and some mammals are amazingly resistant to bacterial infections due to their innate immununity. Antibacterial peptides synthesized by these creatures upon detection of bacteria are known to play an important role in their innate immunity. These antimicrobial peptides are usually basic in character and are composed of 20–40 amino acid residues. Since RPL41 is a 25 amino acids peptide that consists of 68% of basic amino acid residues, its potential antibacterial effect was studied. The inventor found that RPL41 was able to inhibit the growth of *Escherichia coli* at a concentration of 1 µM.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,870,287
U.S. Pat. No. 5,354,855
U.S. Pat. No. 5,359,046
U.S. Pat. No. 5,440,013
U.S. Pat. No. 5,446,128
U.S. Pat. No. 5,475,085
U.S. Pat. No. 5,618,914
U.S. Pat. No. 5,633,016
U.S. Pat. No. 5,670,155
U.S. Pat. No. 5,672,681
U.S. Pat. No. 5,674,976
U.S. Pat. No. 5,710,245
U.S. Pat. No. 5,760,395
U.S. Pat. No. 5,795,715
U.S. Pat. No. 5,798,339
U.S. Pat. No. 5,824,348
U.S. Pat. No. 5,840,833
U.S. Pat. No. 5,859,184
U.S. Pat. No. 5,929,237
Ahmed et al., *J. Cell Biochem. Suppl.*, 35:130–135, 2000.
Amsterdam et al., *PLoS. Biol.*, 2:E139, 2004.
Baichwal and Sugden, In: *Gene Transfer*, Kucherlapati (Ed.), NY, Plenum Press, 117–148, 1986.
Bakhshi et al., *Cell*, 41(3):899–906, 1985.
Bakke et al., *Cell*, 63(4):707–716, 1990.
Barany and Merrifield, In: *The Peptides*, Gross and Meienhofer (Eds.), Academic Press, NY, 1–284, 1979.
Becker-Hapak et al., *Methods*, 24:247–256, 2001.
Bedzyk et al., *J. Biol. Chem.*, 265(30):18615–18620, 1990.
Benvenisty and Neshif, *Proc. Natl. Acad. Sci. USA*, 83(24):9551–9555, 1986.
Brizel, *Semin. Radiat. Oncol.*, 8(4):237–246, 1998.
Burbage et al., *Leuk Res.*, 21(7):681–690, 1997.
Caldas et al., *Nat. Genet.*, 8(1):27–32, 1994.
Capaldi et al., *Biochem. Biophys. Res. Comm.*, 74(2):425–433, 1977.
Caplen et al., Gene, 252(1–2):95–105, 2000.
Carter and Flotte, *Curr. Top Microbiol. Immunol.*, 218:119–144, 1996.
Chatterjee, et al., *Ann. N.Y. Acad. Sci.*, 770:79–90, 1995.
Chaudhary et al., *Proc. Natl. Acad. Sci. USA*, 87(3):1066–1070, 1990.
Chen and Okayama, *Mol. Cell Biol.*, 7(8):2745–2752, 1987.
Cheng et al., *Cancer Res.*, 54(21):5547–5551, 1994.
Cleary and Sklar, *Proc. Natl. Acad. Sci. USA*, (21):7439–7443, 1985.
Cleary et al., *J. Exp. Med.*, 164(1):315–320, 1986.
Coffin, In: *Virology*, Fields et al. (Eds.), Raven Press, NY, 1437–1500, 1990.
Coupar et al., *Gene*, 68:1–10, 1988.
Curran, *Semin. Radiat. Oncol.*, 8(4Suppl):2–4, 1998.
Denicourt and Dowdy, *Trends Pharmacol. Sci.*, 24:216–218, 2003.
Dubensky et al., *Proc. Natl. Acad. Sci. USA*, 81:7529–7533, 1984.
Elbashir et al., *Nature*, 411(6836):494–498, 2001.
el-Kareh and Secomb, *Crit. Rev. Biomed. Eng.*, 25(6):503–571, 1997.
EPO 0273085
Erlandsson, *Cancer Genet. Cytogenet.*, 104(1):1–18, 1998.
Faust et al., *Head Neck*, 22:341–346, 2000.
Fechheimer, et al., *Proc Natl. Acad. Sci. USA*, 84:8463–8467, 1987.
Ferkol et al., *FASEB J.*, 7:1081–1091, 1993.
Ferrari et al., *J. Virol.*, 70(5):3227–3234, 1996.
Fire et al., *Nature*, 391(6669):806–811, 1998.
Fisher et al., *Hum. Gene Ther.*, 7(17):2079–2087, 1996.
Flotte and Carter, *Gene Ther.* 2(6):357–362, 1995.
Flotte et al., *Proc. Natl. Acad. Sci. USA*, 90(22):10613–10617, 1993.

Forster and Symons, *Cell,* 49(2):211–220, 1987.
Fraley et al., *Proc. Natl. Acad. Sci. USA,* 76:3348–3352, 1979.
Futaki et al., *J. Mol. Recognit.,* 16:260–264, 2003.
Gerlach et al., *Nature (London),* 328:802–805, 1987.
Ghosh and Bachhawat, In: *Liver Diseases, Targeted Diagnosis and Therapy Using Specific Receptors and Ligands,* Wu et al. (Eds.), Marcel Dekker, NY, 87–104, 1991.
Goodman et al., *Blood,* 84(5):1492–1500, 1994.
Gopal, *Mol. Cell Biol.,* 5:1188–1190, 1985.
Graham and Van Der Eb, *Virology,* 52:456–467, 1973.
Grishok et al., *Science,* 287:2494–2497, 2000.
Harland and Weintraub, *J. Cell Biol.,* 101(3):1094–1099, 1985.
Harlow et al., *Mol. Cell Biol.,* 5(7):1601–1610, 1985.
Hay et al., *J. Molec. Biology,* 175:493–510, 1984.
Hearing and Shenk, *J. Molec. Biology,* 167:809–822, 1983.
Hearing et al., *J. Virology,* 67:2555–2558, 1987.
Ho et al., *Environ. Health Perspect.,* 106(5):1219–1228, 1998.
Hollstein et al., *Science,* 253(5015):49–53, 1991.
Hussussian et al., *Nat. Genet.,* 8(1):15–21, 1994.
Johannesson et al. *J. Med. Chem.,* 1999 Nov 4; 42(22): 4524–37, 1999.
Johnson et al., In: *Biotechnology And Pharmacy,* Pezzuto et al. (Eds.), Chapman and Hall, NY, 1993.
Joyce, *Nature,* 338:217–244, 1989.
Kamb et al., *Science,* 2674:436–440, 1994.
Kaneda et al., *Science,* 243:375–378, 1989.
Kaplitt et al., *Methods,* 10(3):343–350, 1996.
Kaplitt et al., *Nat Genet,* 8(2):148–54, 1994.
Kasai et al., *J. Histochem. Cytochem.,* 51:567–574, 2003.
Kato et al, *J. Biol. Chem.,* 266:3361–3364, 1991.
Kerr et al., *Br. J. Cancer,* 26(4):239–257, 1972.
Kessler et al., *Proc. Natl. Acad. Sci. USA,* 93(24):14082–14087, 1996.
Ketting et al., *Cell,* 99(2):133–141, 1999.
Kim and Cech, *Proc. Natl. Acad. Sci. USA,* 84:8788–8792, 1987.
Klaudiny et al., *Biochem. Biophys. Res. Commun.,* 187(2): 901–906, 1992.
Klein et al., *Nature,* 327:70–73, 1987.
Koeberl et al., *Proc. Natl. Acad. Sci. USA,* 94(4):1426–1431, 1997.
Kolmel, *J. Neurooncol.,* 38(2–3):121–125, 1998.
Kubota et al., *Biochem. Biophys. Res. Commun.,* 162(3): 963–970, 1989.
Kyte and Doolittle, *J. Mol. Biol.,* 157(1):105–132, 1982.
Lanford et al., *Cell,* 46(4):575–582, 1986.
Lee et al., *Biochem. Biophys. Res. Commun.,* 238(2):462–467, 1997.
Letourneur et al., *Cell,* 69(7):1143–1157, 1992.
Levrero et al., *Gene,* 101:195–202, 1991.
Lidor et al., *Am. J. Obstet. Gynecol.,* 177(3):579–585, 1997.
Litchfield et al., *FEBS Lett.,* 261(1): 117–120, 1990.
Mangray and King, Front Biosci., 3:D1148–1160, 1998.
Mann et al., *Cell,* 33:153–159, 1983.
Massuda et al., *Proc. Natl. Acad. Sci. USA,* 94(26):14701–14706, 1997.
Mayer et al., *Radiat. Oncol. Investig.,* 6(6):281–288, 1998.
McCown et al., *Brain Res,* 713(1–2):99–107, 1996.
Merrifield, *Science,* 232(4748):341–347, 1986.
Mizukami et al., *Virology,* 217(1):124–130, 1996.
Montgomery et al., *Proc. Natl. Acad. Sci. USA,* 95:15502–15507, 1998.
Mougin et al., *Ann. Biol. Clin.,* (Paris) 56(1): 21–8, 1998.
Munro et al., *Cell,* 48(5):899–907, 1987.
Nicolas and Rubenstein, In: *Vectors: A survey of molecular cloning vectors and their uses,* Rodriguez and Denhardt (Eds.), Stoneham: Butterworth, 494–513, 1988.
Nicolau and Sene, *Biochim. Biophys. Acta,* 721:185–190, 1982.
Nicolau et al., *Methods Enzymol.,* 149:157–176, 1987.
Nobri et al., *Nature (London),* 368:753–756, 1995.
Ohara, *Gan To Kagaku Ryoho,* 25(6): 823–8, 1998.
Okamoto et al., *Proc. Natl. Acad. Sci. USA,* 91(23):11045–11049, 1994.
Orlow et al., *Cancer Res,* 54(11):2848–2851, 1994.
Paskind et al., *Virology,* 67:242–248, 1975.
PCT Appln. WO 00/44914
PCT Appln. WO 01/36646
PCT Appln. WO 01/68836
PCT Appln. WO 84/03564
PCT Appln. WO 99/32619
Perales et al., *Proc. Natl. Acad. Sci. USA,* 91:4086–4090, 1994.
Ping et al., *Microcirculation,* 3(2):225–228, 1996.
Potter et al., *Proc. Natl. Acad. Sci. USA,* 81:7161–7165, 1984.
Radler et al., *Science,* 275:810–814, 1997.
Reese and Betts, In: *A Practical Approach to Infectious Diseases,* ($3^{rd}$ Ed.), Boston, Little Brown, 1991.
Remington's Pharmaceutical Sciences, 18th Ed. Mack Printing Company, 1990.
Renan, *Radiother. Oncol.,* 19:197–218, 1990.
Ridgeway, In: *Vectors: A survey of molecular cloning vectors and their uses,* Rodriguez and Denhardt (Eds.), Stoneham:Butterworth, 467–492, 1988.
Rippe et al., *Mol. Cell Biol.,* 10:689–695, 1990.
Roux et al., *Proc. Natl. Acad. Sci. USA,* 86:9079–9083, 1989.
Samulski et al., *J. Virol.,* 61(10):3096–3101, 1987.
Sarver et al., *Science,* 247:1222–1225, 1990.
Scanlon et al., *Proc. Natl. Acad. Sci. USA,* 88:10591–10595, 1991.
Schwarze et al., *Trends Cell Biol.,* 10:290–295, 2000.
Seldin and Leder, *Science,* 267:894–897, 1995.
Serrano et al., *Nature,* 366:704–707, 1993.
Serrano et al., *Science,* 267(5195):249–252, 1995.
Sharp et al., *Science,* 287:2431–2433, 2000.
Sharp, P. A., *Genes. Dev.,* 13:139–141, 1999.
Siomi et al., *Cell,* 55(2):197–209, 1988.
Stanton et al., *Proc. Natl. Acad. Sci. USA,* 83(6):1772–1776, 1986.
Stewart and Young, In: *Solid Phase Peptide Synthesis,* 2d. ed., Pierce Chemical Co., 1984.
Suzuki et al., *Curr. Genet.,* 17(3):185–190, 1990.
Tabara et al., *Cell,* 99(2): 123–132, 1999.
Tam et al., *J. Am. Chem. Soc.,* 105:6442, 1983.
Temin, In: *Gene Transfer,* Kucherlapati (Ed.), NY, Plenum Press, 149–188, 1986.
Tibbetts *Cell,* 12:243–249, 1977.
Tsujimoto and Croce, *Proc. Natl. Acad. Sci. USA,* 83(14): 5214–5218, 1986.
Tsujimoto et al., *Science,* 228(4706):1440–1443, 1985.
Tur-Kaspa et al., *Mol. Cell Biol.,* 6:716–718, 1986.
Vita et al., *Biopolymers,* 47:93–100, 1998.
Wagner et al., *Proc. Natl. Acad. Sci. USA* 87(9):3410–3414, 1990.
Watt et al., *Proc. Natl. Acad. Sci.,* 83(2):3166–3170, 1986.
Weinberg, *Science,* 254(5035):1138–1146, 1991.
Weisshoff et al., *Eur. J. Biochem.,* 259(3):776–788, 1999.
Wender et al., *Proc. Natl. Acad. Sci. USA,* 97:13003–13008, 2000.

Wong et al., *Gene*, 10:87–94, 1980.
Wu and Wu, *Adv. Drug Delivery Rev.*, 12:159–167, 1993.
Wu and Wu, *Biochemistry*, 27:887–892, 1988.
Wu and Wu, *J. Biol. Chem.*, 262:4429–4432, 1987.

Xiao, et al., *J. Virol.*, 70:8098–8108, 1996.
Yang et al., *Proc. Natl. Acad. Sci. USA*, 87:9568–9572, 1990.
Yellon et al., *Cardiovasc Res.*, 26(10):983–987, 1992.

---

What is claimed is:

1. A method of inducing apoptosis in a cancer cell comprising contacting said cancer cell with an RPL41 peptide (SEQ ID NO: 1).

2. A method of treating a subject with cancer comprising administering to said subject a pharmaceutically effective amount of an RPL41 peptide (SEQ ID NO: 1).

* * * * *

SEQUENCE LISTING

<160> NUMBER OF SEQ ID NOS: 9

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Met Arg Ala Lys Trp Arg Lys Lys Arg Met Arg Arg Leu Lys Arg Lys
 1               5                  10                  15

Arg Arg Lys Met Arg Gln Arg Ser Lys
            20                  25

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
atgagagcca agtggaggaa gaagcgaatg cgcaggctga agcgcaaaag aagaaagatg      60
aggcagaggt ccaagtaa                                                   78

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Lys Ser Arg Gln Arg Met Lys Arg Arg Lys Arg Lys Leu Arg Arg Met
 1               5                  10                  15

Arg Lys Lys Arg Trp Lys Ala Arg Met
            20                  25

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cgcagagtac gcggg                                                      15

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic -continued

```
      Primer

<400> SEQUENCE: 5
ccatagacat ctgacctcgg cac                                            23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gtcccacaac ttgtagccag catc                                           24

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Arg Arg Arg Asp Asp Asp Ser Asp Asp Asp
 1               5                  10

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Lys Ala Arg Met Arg Met Lys Arg Lys Leu Arg Lys Arg Met Arg Lys
 1               5                  10                  15

Arg Gln Arg Ser Arg Lys Trp Lys Arg
            20                  25

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Met Leu Ile Ser Ser Gly Leu Lys Asp Gly Ile Arg Ser Gly Ile
 1               5                  10                  15
```